United States Patent [19]
Tang et al.

[11] Patent Number: 5,861,268
[45] Date of Patent: Jan. 19, 1999

[54] METHOD FOR INDUCTION OF TUMOR CELL APOPTOSIS WITH CHEMICAL INHIBITORS TARGETED TO 12-LIPOXYGENASE

[75] Inventors: Dean G. Tang, Troy; Kenneth V. Honn, Grosse Pointe Woods, both of Mich.

[73] Assignee: Biomide Investment Limited Partnership, Grosse Pointe Farms, Mich.

[21] Appl. No.: 652,369

[22] Filed: May 23, 1996

[51] Int. Cl.$^6$ ........................................... C12Q 1/26
[52] U.S. Cl. ........................ 435/25; 435/4; 435/183; 435/975
[58] Field of Search ............... 435/183, 6, 975, 435/4, 25; 514/327, 54; 530/350; 424/85.8; 546/216

[56] References Cited

U.S. PATENT DOCUMENTS

| | | | |
|---|---|---|---|
| 2,868,691 | 1/1959 | Panoush et al. | 167/54 |
| 3,095,355 | 6/1963 | Abramson | 167/54 |
| 5,234,953 | 8/1993 | Marnett et al. | 415/327 |
| 5,238,832 | 8/1993 | Johnson et al. | 435/183 |
| 5,292,884 | 3/1994 | Honn et al. | 546/216 |

OTHER PUBLICATIONS

Tang et al (May 28, 1996), Proc. Nat'l. Acad. USA, vol. 93, No. 11, pp. 5241–5246, "Arachidonate lipoxygenases as essential regulators of cell survival and apoptosis".
Chang et al (1992), vol. 188, No. 2, pp. 538–546, Biochemed and Biophysical Research Communications, "Cell Killing and Induction of Mongenous Super Oxide Dismutase by Tumor Necrosis Factor–λ is Mediated By Lipoxygenase Metabolites of Arachidonic Acid".
Honn et al., "12–Lipoxygenases and 12(S)–HETE: role in cancer metastasis," Cancer and Metastasis Reviews 1994, 13, 365–396, 1994.
Smith et al., "Eicosanoid Effects on Cell Proliferation in Vitro: Relevance to Athenoslenosis," Prosta Glandins Leukotuienes and Med. 1984, 16, 1–10, 1984.
Liu et al., "Lipoxygenase Metabolites of Anachidonic and Linoleic Acids Modulate the Adhesion of Tumor Cells to Endothelium via Regulation of Protein Kinese C," Cell Regul. 1991, 2, 1045–1055, 1991.
Funk, C. D., et al., Proc. Natl. Acad. Sci. 89:3962–3966 (1992).
Marnett, L. J., et al., Adv. Prostaglandin Thromboxand Leukotriene REs. 21:895–900 (1990).
DeMarzo, N., et al., J. Physiol. 262:L198–L207 (1992).
Watanabe, S., et al., Eur. J. Biochem. 212:605–612 (1993).
Freire–Moar, J., et al., Biochem. Biophys. Acta. 1254:112–116 (1995).
Skouteris, G.G., et al., Biochem. Biophys. REs. Commun., 178:1240–1246 (1991).
Nolan, R.D., et al., Mol. Pharmacol. 33:650–656 (1988).
Bailey, J.M., et al., Cell Immunol., 67:112–120 (1982).
Chan, J. M., et al., Invest Dermatol. 85:333–334 (1985).
Kragballe, K., et al., Arch. Dermatol. Res. 278:449–453 (1986).
Bandyopadhyay, G. K., et al., J. Biol. Chem., 263:7567–7573 (1988).
Yamaja Setty, B. N., et al., J. Biol. Chem., 262:17613–17622 (1987).
Dethlefsen, S. M., et al., Exp. Cell Res. 212:262–273 (1994).
Lysz, T.W., et al., Cell Growth & Differ., 5:1069–1076 (1994).
Nadler, R.D., et al., J. Clin. Invest., 80:1763–1769 (1987).
Honn, K. V., et al., Cancer Metastasis Rev. 11:353–375 (1992).
Honn, K. V. et al., Seminar Thromb. Hemost., 18:392–415 (1992).
Honn, K. V., et al., Cancer Metastasis REv. 13:365–396 (1994).
Spector, A. A., et al., Prog. Lipid Res. 27:271–323 (1988).
Tang, D.G., et al., Annals New York Acad. Sci. 744:199–215 (1994).
Tang, D. G., et al., Biochem. Biophys. Res. Commun. 211:462–468 (1995).
Tang, D. G., et al., J. Cell Sci. 108: 2629–2644 (1995).
Brown, D. M., et al., Clin. Immunol. Immunopathol. 63:221–229 (1992).
Kim, I–K, et al., FEBS Lett. 321:209–214 (1993).
Ushikubi, F., et al., J. Exp. Med. 178: 1825–1830 (1993).
Shiff, S. J., et al., J. Clin. Invest. 96:491–503 (1995).
Piazza, G. A., et al., Cancer Res. 55: 3110–3116 (1995).
Shiff, S.J., et al., Exp. Cell Res. 222:179–188 (1996).
Lu, X., et al., Proc. Natl. Acad. Sci. 92:7961–7965 (1995).
Tsujii, M., and R. DuBois, Cell 83:493–501 (1995).
Sandstrom, et al., J. Biol. Chem. 269:798–802 (1994).
O'Donnell, V.B., et al., Biochem. J. 310:133–141 (1995).
Anderson, K.M., et al., Prosta. Leuko. Essent. Fat. Acids 48:323–326 (1993).
Avis, I.M., et al., J. Clin. Invest. 97:806–813 (1996).

*Primary Examiner*—Gary E. Hollinden
*Assistant Examiner*—Dameron Jones
*Attorney, Agent, or Firm*—Ian C. McLeod

[57] ABSTRACT

A method and test kit for determining tumor cell apoptosis by inhibition of 12-lipoxygenase is described. A method for selectively inducing tumor cell apoptosis by inhibiting 12-lipoxygenase is also described. The preferred compounds are selected from the group consisting of a cyclic hydroxamic acid; and an aryl aliphatic acid; nordihydro guaiaretic acid (NDGA) and N-benzyl-N-hydroxy-5-phenylpentanamide (BHPP).

34 Claims, 10 Drawing Sheets

FIG. 3A 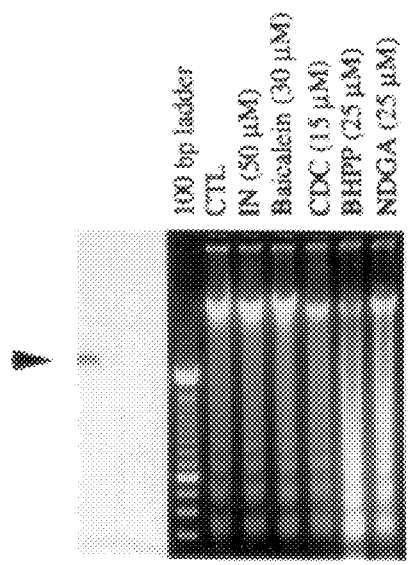 FIG. 3B 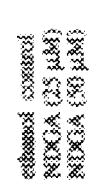 FIG. 3C 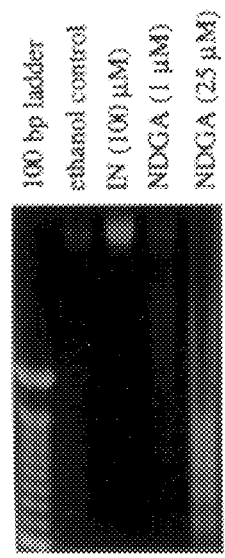
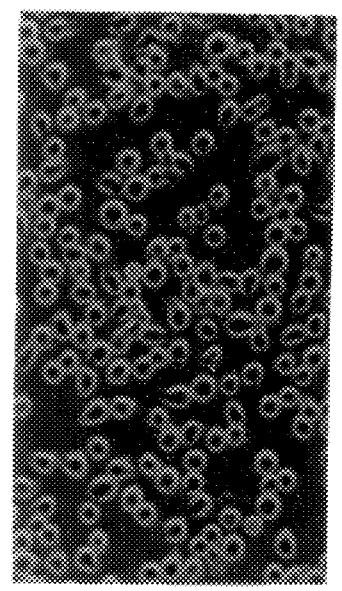 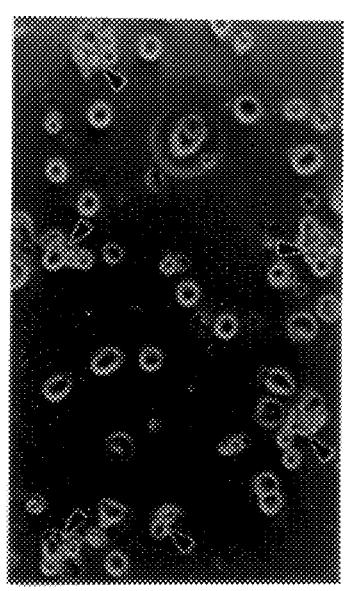 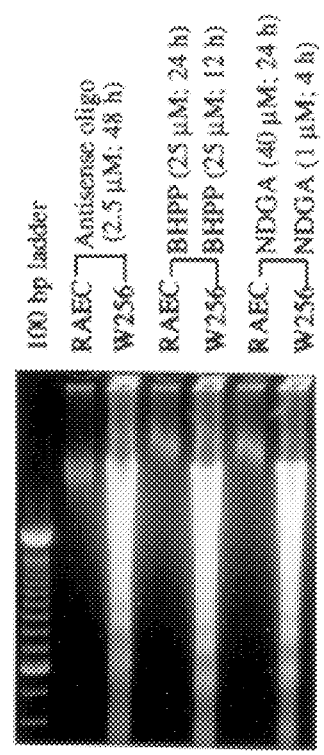
FIG. 3D  FIG. 3E  FIG. 3F

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
                ( A ) LENGTH: 18
                ( B ) TYPE: Amino Acid
                ( C ) STRANDEDNESS: Single
                ( D ) TOPOLOGY: Linear ( i i ) MOLECULE TYPE:
                ( A ) DESCRIPTION: DNA primer for segment
                        of 12- lipoxygenase.

( i i i ) HYPOTHETICAL: No ( i v ) ANTI-SENSE: No ( v i ) ORIGINAL SOURCE:
                ( A ) ORGANISM: human ( v i i ) IMMEDIATE SOURCE:
                ( A ) LIBRARY: Genomic ( x i ) SEQUENCE DESCRIPTION: SEQ ID NO: 1:

Trp Thr Leu Lys Ala Gly Ala Leu Glu Met Ala Leu
                    5                       1 0
Lys Arg Val Tyr Thr Leu
                1 5

( 2 ) INFORMATION FOR SEQ ID NO:2:

( i ) SEQUENCE CHARACTERISTICS:
                ( A ) LENGTH: 29 Bases
                ( B ) TYPE: Nucleic Acid
                ( C ) STRANDEDNESS: Single
                ( D ) TOPOLOGY: Linear ( i i ) MOLECULE TYPE:
                ( A ) DESCRIPTION: DNA primer for
                        a segment of 12-lipoxygenase.

( i i i ) HYPOTHETICAL: No ( i v ) ANTI-SENSE: No ( v i ) ORIGINAL SOURCE:
                ( A ) ORGANISM: Human ( v i i ) IMMEDIATE SOURCE:
                ( A ) LIBRARY: Genomic ( x i ) SEQUENCE DESCRIPTION: SEQ ID NO: 2:

GGATCCTAAT ACGACTCACT ATAGGGAGG                                              2 9

( 2 ) INFORMATION FOR SEQ ID NO:3:

( i ) SEQUENCE CHARACTERISTICS:
                ( A ) LENGTH: 18 Bases
                ( B ) TYPE: Nucleic Acid
                ( C ) STRANDEDNESS: Single
                ( D ) TOPOLOGY: Linear ( i i ) MOLECULE TYPE:
                ( A ) DESCRIPTION: DNA primer for a
                        segment of 12-lipoxygenase.

( i i i ) HYPOTHETICAL: No ( i v ) ANTI-SENSE: Yes ( v i ) ORIGINAL SOURCE:
                ( A ) ORGANISM:

( v i i ) IMMEDIATE SOURCE:
                ( A ) LIBRARY: Genomic ( x i ) SEQUENCE DESCRIPTION: SEQ ID NO: 3:

```
CTGGACTTTG AATGGACA                                                    18
```

(2) INFORMATION FOR SEQ ID NO:4:

(i) SEQUENCE CHARACTERISTICS:
        (A) LENGTH: 29 Bases
        (B) TYPE: Nucleic Acid
        (C) STRANDEDNESS: Single
        (D) TOPOLOGY: Linear (ii) MOLECULE TYPE:
        (A) DESCRIPTION: DNA primer for a
            segment of 12-lipoxygenase (iii) HYPOTHETICAL: No (iv) ANTI-SENSE: Yes (vi) ORIGINAL SOURCE:
        (A) ORGANISM: Human (vii) IMMEDIATE SOURCE:
        (A) LIBRARY: Genomic (xi) SEQUENCE DESCRIPTION: SEQ ID NO: 4:

```
CTCGAGCTAT TCTATAGTGT CACCTAAAT                                        29
```

(2) INFORMATION FOR SEQ ID NO:5:

(i) SEQUENCE CHARACTERISTICS:
        (A) LENGTH: 18 Bases
        (B) TYPE: Nucleic Acid
        (C) STRANDEDNESS: Double
        (D) TOPOLOGY: Linear (ii) MOLECULE TYPE:
        (A) DESCRIPTION: DNA encoding a
            segment of 12-lipoxygenase.

(iii) HYPOTHETICAL: No (iv) ANTI-SENSE: No (vi) ORIGINAL SOURCE:
        (A) ORGANISM: Human (vii) IMMEDIATE SOURCE:
        (A) LIBRARY: Genomic (xi) SEQUENCE DESCRIPTION: SEQ ID NO: 5:

```
CTCAGGAGGG TGTAAACA                                                    18
```

(2) INFORMATION FOR SEQ ID NO:6:

(i) SEQUENCE CHARACTERISTICS:
        (A) LENGTH: 18 Base Pairs
        (B) TYPE: Nucleic Acid
        (C) STRANDEDNESS: Single
        (D) TOPOLOGY: Linear (ii) MOLECULE TYPE:
        (A) DESCRIPTION: DNA encoding a
            segment of 12-lipoxygenase.

(iii) HYPOTHETICAL: No (iv) ANTI-SENSE: No (vi) ORIGINAL SOURCE:
        (A) ORGANISM: Human (vii) IMMEDIATE SOURCE:
        (A) LIBRARY: Genomic ( x i ) SEQUENCE DESCRIPTION: SEQ ID NO: 6:

CTCAGGAGGG TGTAAACA 1 8

METHOD FOR INDUCTION OF TUMOR CELL APOPTOSIS WITH CHEMICAL INHIBITORS TARGETED TO 12-LIPOXYGENASE

BACKGROUND OF THE INVENTION

1. Field of the Invention

The present invention relates to methods for the identification and use of chemical compounds that can selectively kill tumor cells by inducing cell apoptosis. Apoptosis is a natural process for normal cells and means programmed cell death. Tumor cells can avoid apoptosis and thus are able to survive and develop in the body. The method is significant in cancer therapy, since it can detect novel candidate chemotherapeutic drugs that could be used for the clinical treatment of cancer patients. In particular, the present invention relates to the methods using chemical compounds that are targeted to inhibit 12-lipoxygenase in inducing the tumor cell apoptosis.

2. Description of Related Art

Normal tissue homeostasis is maintained by balanced cell proliferation and cell death, which occurs most frequently in the form of apoptosis or programmed cell death. Tumor cells differ significantly from their normal counterparts with respect to the control of cell growth and proliferation. Most tumor cells demonstrate a self-dominant growth pattern either due to their abnormal response to environmental stimuli (hormones, growth factors, cytokines, etc.) or due to an autonomous nature of growth (i.e., autocrine stimulation). Tumor cells also demonstrate abnormal apoptotic responses. Many factors have been shown to regulate apoptosis, including (i) growth factors and growth factor receptors such as retinoid acid, interleukin-3, stem cell factor, interferon-$\gamma$, erythropoietin, NGF/NGF (nerve growth factor) receptor, TNF-$\alpha$/Fas (tumor necrosis factor-$\alpha$), steel factor/Kit receptor, TGF-$\beta$/TGF (transforming growth factor) receptor, insulin, EGF/EGFR (epidermal growth factor), IGF-1/IGF (insulin-like growth factor) receptor, and PDGF/PDGF (platelet-derived growth factor receptor); (ii) intracellular signal transducers such as protein kinase C, PI-3 (phosphoinositol-3) kinase, Ras and GTPase, PLC-$\gamma$ (phospholipase C-$\gamma$), tyrosine kinases and protein phosphatases, lipid signaling molecules such as eicosanoids, sphingosine, ceramide, and $Ca^{2+}$; (iii) cell cycle regulators exemplified by Cdc-2 and E2F-1; (iv) reactive oxygen species or other free radicals; (v) extracellular matrix regulators/cell adhesion molecules (extracellular matrix proteins such as fibronectin and transmembrane integrin receptors) ; and (vi) specific endonucleases such as $Ca^{2+}$- and $Mg^{2+}$-dependent DNase and cytoplasmic proteases typified by ICE (interleukin 1$\beta$-converting enzyme) family. Many of these regulators have been associated with various human malignancies and apoptosis. For example, studies on human tumors including neuroblastoma, glioma, lymphoma, breast carcinoma, colorectal adenocarcinoma, melanoma and gastrointestinal malignancies have demonstrated an overall positive correlation between increased expression of Bcl-2 (or Bcl-$X_L$) or decreased expression of Bax and uncontrolled tumor cell growth, and, in some cases, with tumor progression and a poor prognosis of cancer patients. Another example is p53, a phosphoprotein known to modulate gene transcription, police cell cycle checkpoints, control DNA replication and repair, and maintain genomic stability. Wild type p53 also positively regulates apoptosis. p53 gene mutations have been linked to attenuated apoptosis in multiple cancers represented by Wilms' tumor, colon cancer, cervical carcinoma and breast cancer. Since apoptosis plays a critical role in multiple steps (transformation, progression and survival of metastases) of tumorigenesis as well as in tumor cells' response to chemotherapeutic drugs or radiation therapy, many chemoprevention and therapeutic regimens attempting to manipulate apoptotic process have been proposed to aid in the clinical treatment of cancer patients (Fesus, L., et al., J. Cell Biochem. 22:151–161 (1995); Lotan, R., J. Natl. Cancer Inst. 87:1655–1657 (1995); van Zandwijk, N., J. Cell Biochem. 22:24–32 (1995)).

Arachidonic acid (AA) is an essential component of the cell membrane phospholipids. AA released through the action of phospholipase $A_2$ is metabolized via three major biochemical pathways: (i) the cyclooxygenase (COX) pathway leading to the generation of prostaglandins, prostacyclin, and thromboxane; (ii) the lipoxygenase (LOX) pathway giving rise to various hydroperoxy (HPETEs) and hydroxy (HETEs) fatty acids as well as leukotrienes; and (iii) the P450-dependent epoxygenase pathway generating EETs. Mammalian LOX display varying degrees of substrate specificity for insertion of molecular oxygen into arachidonic acid at carbon positions 5, 12, and 15. The enzymes, based on the abundance of the majority products have thus been termed 5, 12, and 15 lipoxygenases, respectively. The 12-LOX catalyzes the transformation of AA into 12(S)-hydroperoxyeicosatetraenoic acid (12-HPETE) and its 12(S)-hydroxy derivatives [i.e. 12(S)-HETE]. Three types of mammalian 12-LOX enzymes have so far been reported. The first is human platelet-type 12-lipoxygenase expressed normally in platelets, HEL (human erythroleukemia) cells, and umbilical vein endothelial cells (Funk, C. D., et al., Proc. Natl. Acad. Sci. 87:5638–5642 (1990); Funk, C. D., et al., Proc. Natl. Acad. Sci. 89:3962–3966 (1992)). Platelet-type 12-LOX metabolizes only AA (but not C-18 fatty acids such as linoleic acid) to form exclusively 12(S)-HETE (Funk, C. D., et al., Proc. Natl. Acad. Sci. 87:5638–5642 (1990) Marnett, L. J., et al., Adv. Prostaglandin Thromboxane Leukotriene Res. 21:895–900 (1990)). The second is porcine leukocyte-type 12-LOX which metabolizes both AA and linoleic acid thus generating 12(S)-HETE as well as small amounts of 15(S)-HETE (Hada, T., et al., Biochim. Biophys. Acta 1083–1087 (1991)). The third type of 12-LOX (sometimes termed epithelial 12-lipoxygenase) has been isolated from bovine tracheal epithelial cells (De Marzo, N., et al., J. Physiol. 262:L198–L207 (1992)); rat brain (Watanabe, S., et al., Eur. J. Biochem. 212:605–612 (1993)), and murine macrophages (Freier-Moar, J., et al., Biochim. Biophys. Acta., 1254:112–116 (1995)), which shares more homology with 15-LOX and leukocyte-type 12-LOX than with platelet-type 12-LOX. This type of 12-LOX, like reticulocyte 15-LOX and leukocyte-type 12-LOX, catalyzes the formation of both 12(S)-HETE and 15(S)-HETE.

The role of AA metabolites in regulating cell proliferation has been recognized for more than two decades. Numerous studies have demonstrated a strong positive correlation between growth factor- (EGF, insulin, PDGF, etc.) promoted cell proliferation and generation of various COX products, primarily prostaglandins (Skouteris, G. G., et al., Biochem. Biophys. Res. Commun., 178:1240–1246 (1991); Nolan, R. D., et al., Mol. Pharmacol. 33:650–656 (1988); Smith, D. L., et al., Prostaglandins Leukotrienes Med., 16:1–10 (1984)). Similarly, it has been found that various eicosanoids derived from LOX pathways as well as epoxygenase pathways of AA metabolism play an essential role in mediating the growth factor-stimulated normal cell and tumor cell growth. Examples include 15-HETE as a mitogenic regulator of T-lymphocyte (Bailey, J. M., et al., Cell Immunol., 67:112–120 (1982)), 12-HETE and $LTB_4$ as growth stimulators of epidermal cells (Chan, C., et al., J. Invest. Dermatol., 85:333–334 (1985)), 12-HETE stimulation of keratinocyte DNA synthesis (Kragballe, K., et al., Arch. Dermatol. Res., 278:449–453 (1986)), 15-/12-HETEs as mediators of insulin and EGF-stimulated mammary epithelial cell proliferation (Bandyopadhyay, G. K., et al., J. Biol. Chem., 263:7567–7573 (1988)) and as synergistic effectors of bFGF- (basic fibroblast growth factor) and PDGF- regulated growth of vascular endothelial cells and smooth muscle cells (Yamaja Setty, B. N., et al., J. Biol. Chem., 262:17613–17622 (1987); Dethlefsen, S. M., et al., Exp. Cell Res., 212:262–273 (1994)), 12(S)-HETE as a regulator of EGF- and insulin-stimulated DNA synthesis and protooncogene expression in lens epithelial cells (Lysz, T. W., et al., Cell Growth & Differ., 5:1069–1076 (1994)) and as the mediator of angiotensin II-induced aldosterone synthesis in adrenal glomerulosa cells (Nadler, R. D., et al., J. Clin. Invest., 80:1763–1769 (1987)).

The present inventors have long been interested in the modulatory role of various eicosanoids in tumorigenesis and metastatic process. Early work demonstrated an important function for prostacyclin ($PGI_2$) and thromboxane ($TxA_2$), two major cyclooxygenase (COX) products of AA metabolism derived primarily from vascular endothelial cells and platelets, respectively, in regulating the hematogenous spreading of malignant tumor cells (Honn, K. V., et al., Science 212:1270–1272 (1981); reviewed in Schneider et al., Cancer metastasis Rev. 13:349–364 (1994)). Later, systematic in vitro and in vivo studies have led to the discovery that many LOX metabolites also play a key role in modulating the phenotypic properties of tumor cells as well as tumor cell-vasculature interactions (Reviewed in Honn, K. V., et al., Cancer Metastasis Rev. 11:353–375 (1992); Honn, K. V., and D. G. Tang, Seminar Thromb. Hemost., 18:392–415 (1992); Tang, D. G. and K. V. Honn, Invasion Metastasis 14:109–122 (1995)). Prominently, a small hydroxy fatty acid molecule derived from the LOX pathway of AA metabolism, i.e., 12(S)-HETE [12(S)-hydroxyeicosatetraenoic acid], has been observed to possess a wide-spectrum of biological activities including, among others, inducing platelet aggregation, stimulating insulin secretion, suppressing renin production, chemoattracting leukocytes, facilitating macrophage adhesion, inhibiting prostacyclin biosynthesis by vascular endothelial cells (Spector, A. A., et al., Prog. Lipid Res. 27:271–323 (1988); Sekiya, K., et al., Biochem. Biophys. Res. Commun. 105:1090–1095 (1982), modulating tumor cell interactions with extracellular matrix, promoting tumor cell motility, facilitating tumor cell release of proteolytic enzyme cathepsin B, reorganizing tumor cell cytoskeleton, promoting tumor cell adhesion on endothelial cells via upregulating integrin expression on tumor cells and/or endothelial cells, and inducing endothelial cell retraction thus enhancing tumor cell extravasation from the vasculature (reviewed in Honn, et al., Seminar Thromb. Hemost. 18:390–413 (1992); Honn, K. V., et al., Cancer Metastasis Rev., 13:365–396 (1994); Tang, D. G. and K. V. Honn, Annals New York Acad. Sci., 744:199–215 (1994); Tang, D. G. and K. V. Honn, Invasion Metastasis 14:109–122 (1995)). Very recently, the inventors have reported 12(S)-HETE as a mitogenic factor for microvascular endothelial cells (Tang, D. G., et al., Biochem. Biophys. Res. Commun. 211:462–468 (1995a)) and a transactivator of integrin αv (Tang, D. G., et al., J. Cell Sci. 108:2629–2644 (1995b)). Significant progress has been made in delineating the molecular mechanisms of the 12(S)-HETE effects. 12(S)-HETE, possibly through binding to a cell surface receptor(s), triggers phosphoinositol lipid hydrolysis (Liu, B., et al., Proc. Natl. Acad. Sci. 92:9323–9327 (1995)) leading to the intracellular activation of protein kinase C (PKC; Liu, B., et al., Cell Regul. 2:1045–1055 (1992)) and/or protein tyrosine kinase (PTK; Tang, D. G., et al., J. Cell. Physiol. 165:291–306 (1995c)). The interactions of these phosphorylated protein kinases with various intracellular molecular targets (e.g., cytoskeletal proteins, adhesion molecules, signaling molecules, etc.) largely explain the versatility of the 12(S)-HETE effects.

Both COX and LOX products of AA metabolism may also be involved in modulating tumor cell survival and apoptosis. Thus, many prostaglandins such as $PGE_2$ (prostaglandin $E_2$) (Brown, D. M., et al., Clin. Immunol. Immunopathol. 63:221–229 (1992) ), $PGA_2$ and $\Delta^{12}$-$PGJ_2$ (Kim, I-K, et al., FEBS Lett. 312:209–214 (1993)) have been shown to induce apoptosis of leukemia or lymphoma cells as well as solid tumor cells. Similarly, $TxA_2$ induces apoptotic cell death of immature thymocytes by binding to the cell surface $TxA_2$ receptors (Ushikubi, F., et al., J. Exp. Med. 178:1825–1830 (1993) ). Interestingly, $PGE_2$ also has been reported to protect cells from apoptosis induction (Goetzel, E. J., et al., J. Immunol. 154:1041–1047 (1995)). On the other hand, various COX inhibitors (NSAID) (Non-steroidal anti-inflammation drugs) have been consistently demonstrated to trigger apoptosis of cultured cells. Thus, indomethacin, sulindac sulfide and sulfone inhibit colon carcinoma cell (HT-29) growth by inducing apoptosis (Shiff, S. J., et al., J. Clin. Invest. 96:491–503 (1995); Piazza, G. A., et al., Cancer Res. 55:3110–3116 (1995); Shiff, S. J., et al., Exp. Cell Res. 222:179–188 (1996)). Likewise, multiple NSAIDs including diflunisal, indomethacin, acemethacin, diclofenac, mefenamic acid, flufenamic acid, niflumic acid, ibuprofen, and carprofen cause apoptosis in chicken embryo fibroblasts (Lu, X., et al., Proc. Natl. Acad. Sci. 92:7961–7965 (1995)). These observations suggest that the COX/COX metabolites may play a dual role in regulating cell survival and apoptosis. Under certain circumstances the COX products (e.g., $PGE_2$ and cyclopentenone prostaglandins) can either directly trigger cell death or mediate apoptosis induced by, e.g., TNF-α (Larrick, J. W., and S. C. Wright, FASEB J. 4:3215–3223 (1990)). In a different scenario, the COX activity/function are critical for cell survival since inhibition with various inhibitors leads to cell death (see above). Consistent with this, overexpression of COX-2 has been observed to confer resistance in rat intestinal epithelial cells to apoptosis induction by butyrate (Tsujii, M., and R. DuBois, Cell 83:493–501 (1995)).

Similar to the COX system, some LOXs and their products may also play a dual regulatory role in cell survival and apoptosis. Exogenous lipid hydroperoxides such as 15-HPETE induces HIV-infected human T cells (Sandstrom, et al., J. Biol. Chem. 269:798–802 (1994)) due to their inability to convert 15-HPETE to 15-HETE owing to a reduction in the glutathione peroxidase activity, LOX metabolites have been proposed as the actual mediators of TNFα-induced apoptosis of multiple cells since LOX inhibitors such as ETYA and NDGA could inhibit its cytotoxicity (Chang, D. J., et al., Biochem. Biophys. Res. Commun. 188:538–546 (1992); O'Donell, V. B., et al., Biochem. J. 310:133–141 (1995)). On the other hand, 5-LOX inhibitors can cause apoptosis of human leukemia blast cells (Anderson, K. M., et al., Prosta. Leuko. Essent. Fat. Acids 48:323–326 (1993)) and interruption of 5-LOX-mediated growth factor signaling inhibits the growth of lung cancer cells due to apoptosis induction (Avis, I. M., et al., J. Clin.

Invest. 97:806–813 (1996)), suggesting that in some cells 5-LOX pathway may function as a critical survival factor.

There has been no literature report relating to the potential role of mammalian 12-LOX in regulating tumor cell survival and apoptosis. Based on extensive studies by the inventors on the role of 12(S)-HETE in regulating tumor cell growth and on the relationship between 12-LOX expression and the metastatic capacity of a variety of tumor cells, it is hypothesized that 12-LOX system may also be involved in regulating tumor cell survival and apoptosis.

OBJECTS

It is therefore an object of the present invention to provide a method for determining tumor cell apoptosis using a candidate compound which inhibits 12-lipoxygenase. Further, it is an object of the present invention to induce apoptosis of tumor cells in the laboratory or in vivo in a mammal using compounds which are positively determined to produce apoptosis in vitro. Further, it is an object of the present invention to provide methods which can be effective in treating tumors. These and other objects will become increasingly apparent by reference to the following description and the drawings.

BRIEF DESCRIPTION OF DRAWINGS

FIG. 1A is a Northern blot. FIG. 1B is a blot using RNase protection assay (RPA). The band indicated with an arrow represents the expected protected fragment of 12-LOX (~75 bp). S, sense probe; A.S., antisense probe. FIG. 1C is a Western blot using polyclonal antibody raised against the 12-LOX whole molecule (left panel) and against sequence-specific peptide (right panel). Arrowheads indicate the ~72 kd 12-LOX protein.

FIG. 2A is a graph showing time- and dose-studies of W256 cell apoptosis induced by BHPP, a 12-LOX-selective inhibitor. Sixty-thousand W256 cells (indicated by the horizontal bar) cultured in 24-well plates were treated with solvent control (ethanol; labeled as "O") or increasing doses of BHPP in regular serum-containing MEM. The experiments were terminated at 24 hours (Day 1), 48 hours (Day 2), and 72 hours (Day 3) after the initiation of treatment. Dead cells were removed and cell survival enumerated with a Coulter counter. Each condition was run in triplicate and the results represent mean±S.E. obtained from three independent experiments. FIG. 2B is a photograph of a gel showing dose and time studies of DNA fragmentation induced by BHPP. FIGS. 2C and 2D are photographs of cells showing morphological alterations of W256 cells after NDGA (2.5 $\mu$M) treatment for 2 hours (2C) or 4 hours (2D). Numerous apoptotic cells with membrane blebbing were seen in the early phase (FIG. 2C, arrowheads) and apoptotic bodies were prevalent in the culture at a later stage (FIG. 2D, arrowheads). Original magnification: x200. Quantitation revealed that at the end of 4 hours treatment, NDGA caused a 60±4.7%, 87±6.8% and 98±3.4% apoptosis at 1.0, 2.5, and 5.0 $\mu$M, respectively.

FIGS. 3A to 3F show that NDGA also induces or enhances apoptotic death of other tumor cells. FIG. 3A is a photograph of a gel showing that NDGA enhances apoptosis of MTLn-3 rat mammary adenocarcinoma cells. The left panel shows the mRNA expression of 12-LOX (~3.0 kb; arrowhead) and the right panel demonstrates the apoptosis-enhancing effect of BHPP (a 12-LOX selective inhibitor; Chen, Y. Q., et al., Cancer Res. 54:1574–1579 (1994)), CDC, baicalein and NDGA. The treatment was for 24 hours. Note there exists very high spontaneous apoptosis in MTLn-3 cells. IN, indomethacin. FIG. 3B is a photograph of a gel showing that NDGA induces apoptosis of RBL-1 (rat basophilic leukemia cells). The treatment was for 24 hours. FIG. 3C is a photograph of a gel showing that NDGA induces apoptotic death of HEL (human erythroleukemia) cells. The treatment was for 12 hours. IN: indomethacin. FIG. 3D and 3E are photographs of cells showing HEL cells treated with ethanol control (3D) or 25 $\mu$M NDGA for 12 hours (3E). The apoptotic cell clusters are indicated by arrowheads. Note some cells demonstrate necrotic features due to the asynchronic induction of apoptosis by NDGA. The original magnification was 200x. FIG. 3F is a photograph of a gel showing different sensitivity of W256 cells and normal endothelial cells (i.e., RAEC; rat aortic endothelial cells; Tang, D. G., et al., Int. J. Cancer 54:102–111 (1993a)) to NDGA, BHPP or a 12-LOX-specific antisense oligo (5'-CTCAGGAGGGTGTAAACA-3'). Isolation of fragmented DNA and agarose gel electrophoresis were performed as described in Materials and Methods.

FIG. 4A-1, control. FIG. 4A-2, 1 $\mu$M NDGAx 24 hours Ac, 25 $\mu$M BHPPx24 hours. FIG. 4B-1, 50 $\mu$M compound 199x24 h. FIG. 4C-1, 50 $\mu$M compound 245x4 h. FIG. 4C-2, 50 $\mu$M compound 243x4 h. FIG. 4C-3, 50 $\mu$M compound 244x4 h. FIG. 4D-1, 50 $\mu$M compound 226x24 h. FIG. 4D-2, 1 $\mu$M compound 312x24 h. FIG. 4D-3, 10 $\mu$M compound 314x4 h. It can be seen that all of these compounds induce apoptosis of W256 cells, but with different efficacies. Apoptotic cells demonstrate typical morphological features including shrunk cell body and membrane blebbings. Original magnification, x200.

FIG. 5A is a photograph of control tumor cells. FIG. 5B is a photograph of apoptotic cells. Apoptotic cells (5B) demonstrate typical membrane blebbings and condensed chromatin. Original magnification, x10,000.

FIG. 6A: lane 1, M.W. marker; lane 2, control (i.e., ethanol-treated W256 cells); lane 3, positive control NDGA (5 $\mu$Mx4 h); lane 4, 25 $\mu$M compound 199x24 h; lane 5, 25 $\mu$M compound 214x24 h. FIG. 6B: W256 cells treated with various compounds at the concentrations and time intervals indicated.

FIG. 8A shows DNA fragmentation assays. Lanes 1–3, human umbilical vein endothelial cells (HUVEC) treated with 50 μM of BHPP (lane 1), compound 199 (lane 2) or compound 314 (lane 3) for 24 h. Lanes 4 and 5, A431 human epidermoid carcinoma cells treated with 25 μM BHPP (lane 4) or compound 314 (lane 5) for 12 h. FIGS. 8B to 8F show examples showing photomicrographs of HUVEC treated with compounds NDGA 199, 214, 312 as indicated. Original magnification, ×200. The cells are undamaged.

DESCRIPTION OF PREFERRED EMBODIMENTS

Figure 1A:
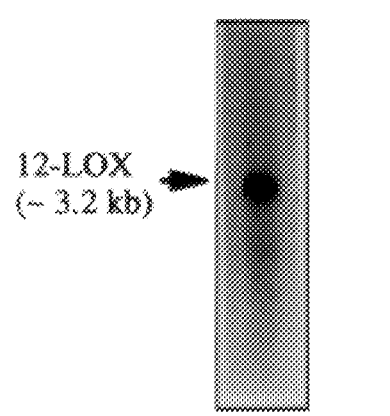
FIGS. 1A, 1B and 1C relate to the expression of platelet-type 12-LOX in W256 cells.

The present invention relates to an in vitro method for determining effectiveness of a compound in producing apoptosis which comprises:

providing tumor cells which are known to produce 12-lipoxygenase;

exposing the tumor cells to a compound which inhibits 12-lipoxygenase which is to be tested in vitro in a culture medium for a period of time; and determining whether cells which have undergone apoptosis as a result of the exposure.

Further, the present invention relates to a method for inducing apoptosis of tumor cells which comprises:

contacting the tumor cells with a 12-lipoxygenase inhibitor until apoptosis is induced, wherein apoptosis is induced in the tumor cells without inducing apoptosis in normal cells.

The present invention also relates to a kit for detecting tumor cell apoptosis by a test compound which is to be tested with normal cells and tumor cells which produce 12-lipoxygenase, which comprises:

(a) a known compound which induces apoptosis in the tumor cells without inducing apoptosis in the normal cells; and (b) detection means for determining that apoptosis has been induced by the test compound as compared to the known compound.

In the in vitro method the cells are exposed to a compound which may induce apoptosis. This can be accomplished by measuring the extent of cell death by using DNA fragmentation, microscopy (light or electron microscope) or flow cytometry.

The cells used are for instance RBL-1 (CRL-1378), HEL (T1B-180) or A431 (CRL-1555). These cell lines have been deposited with the American Type Culture Collection (ATCC) (Rockville, Md.) by third parties. Other cell lines are W256 and MTLn-3 cells which are well known to those skilled in the art and widely available.

The cells are grown in a minimal essential medium (Gibco, Life Technologies, MD), which contains various essential amino acids, vitamins and inorganic components. This culture medium does not interfere with the examination of the cells for apoptosis.

The preferred compounds which induce apoptosis are:

aryl aliphatic acids or derivatives thereof (An aryl aliphatic acid or derivatives thereof of the formula

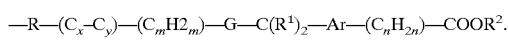

wherein m and n are an integer between 1 and 6;

wherein the pattern of substitution in the aryl ring (Ar) is selected from the group consisting of orth-, meta- and para-, wherein G is selected from the group consisting of O and S;

wherein $(C_x-C_y)$ is selected from the group consisting of ethynylene, cis-vinylene, trans-vinylene, propadienylene, and arylene;

wherein R is selected from the group consisting of heptyl, octyl, nonyl, decyl, undecyl, dodecyl, tridecyl, tetradecyl, phenyl, benzyl, phenethyl, phenylpropyl, phenylbutyl, and phenylpentyl and isomers thereof;

wherein each $R^1$ is independently H or lower alkyl or a combination thereof;

wherein $R^2$ is H, a salt lower alkyl or aralkyl.) as described in U.S. Pat. No. 5,238,832 which is incorporated by reference herein. Also cyclic hydroxamic acids (A cyclic hydroxamic acid of the formula:

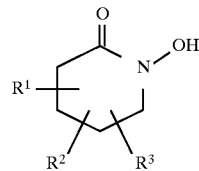

$R^1$, $R^2$ and $R^3$ each, independently, is hydrogen, C1–24 alkyl, C2–24 alkenyl or a group of the formula:

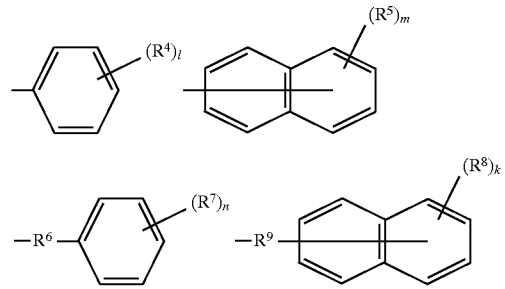

wherein
$R^4$, $R^5$, $R^7$ and $R^8$ each, independently is hydrogen, C1–4 alkyl, C1–4 alkoxy, trifluoromethyl, halogen or nitro;
l is 1–3;
m is 1–3;
n is 1–3;
k is 1–3;
$R^6$ and $R^9$ each, independently is C1–24 alkylene or C2–24 alkenylene;

with the proviso that, more than one of $R^1$, $R^2$ and $R^3$ are not hydrogen at the same time; and the pharmaceutically acceptable salts thereof.) of U.S. Pat. No. 5,234,933, and alpha hydroxamic acids of (A cyclic hydroxamic acid of the formula:

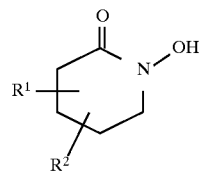

wherein $R^1$ is $C_1$ to $C_{24}$ alkyl and wherein $R^2$ is benzyl.) of U.S. Pat. No. 5,292,884 which are incorporated by reference herein. Other compounds are N-benzyl-N-hydroxy-5-phenylpentanamide (BHPP), baicalein and nordihydro guaiaretic acid (NDGA).

Applications For Pharmaceuticals

Since the compounds of the present invention induce apoptosis by inhibiting 12-lipoxygenase in vitro, it is expected to be useful for prevention and/or treatment of the above disease in mammals including lower animals and humans.

For the purposes described above, the compounds of the present invention may normally be administered systemically or parenterally.

The doses to be administered are determined depending upon age, body weight, symptom, the desired therapeutic effect, the route of administration, and the duration of the treatment, etc. In a human adult, the doses per person per administration are generally between 1 mg and 500 mg, by oral administration, up to several times per day, and between 1 mg and 100 mg, by parenteral administration up to several times per day.

Since the does to be used depend upon various tumors, as mentioned above, there may be a case in which doses are lower than or greater than the ranges specified above.

Solid compositions for oral administration include compressed tablets, pills, dispersible powders, capsules, and granules. In such compositions, one or more of the active compound(s) is or are, admixed with at least one inert diluent (lactose, mannitol, glucose, hydroxypropyl-cellulose, microcrystalline cellulose, starch, polyvinyl pyrrolidone, magnesium metasilicate aluminate etc.). The compositions may also comprise, as is normal practice, additional substances other than inert diluents: e.g., lubricating agents (magnesium stearate, etc.), disintegrating agents (cellulose calcium glycolate, etc.), and assisting agent for dissolving (glutamic acid, aspartic acid, etc.) stabilizing agent (lactose etc.).

The tablets or pills may, if desired, be coated with gastric or enteric material (sugar, gelatin, hydroxypropyl-cellulose or hydroxypropylmethyl cellulose phthalate, etc.).

Capsules include soft ones and hard ones.

Liquid compositions for oral administration include pharmaceutically-acceptable emulsions, solutions, suspensions, syrups, and elixirs. In such compositions, one or more of the active compound(s) is or are admixed with inert diluent(s) commonly used in the art (purified water, ethanol, etc.). Besides inert diluents, such compositions may also comprise adjuvants (wetting agents, suspending agents, etc.), sweeting agents, flavoring agents, perfuming agents and preserving agents.

Other compositions for oral and nasal administration include spray compositions which may be prepared by known methods and which comprise one or more of the active compound(s).

Spray compositions may comprise additional substances other than inert diluents; e.g. preserving agents (sodium sulfite, etc.), isotonic buffer (sodium chloride, sodium citrate, citric acid, etc.).

For preparation of such spray compositions, for example, the method described in U.S. Pat. Nos. 2,868,691 or 3,095,355 may be used.

Injections for parenteral administration include sterile aqueous or non-aqueous solution, suspensions and emulsions. In such compositions, one or more of active compound(s) is or are admixed with at least one inert aqueous diluent(s) (distilled water for injection, physiological salt solution, etc.) or inert non-aqueous diluent(s) (propylene glycol, polyethylene glycol, olive oil, ethanol, POLYSOLBATE 80 (registered trademark) and the like.

Injections may comprise additional substances other than inert diluents: e.g. preserving agents, wetting agents, emulsifying agents, dispersing agents, stabilizing agents (lactose etc.), assisting agents such as for dissolving (glutamic acid, aspartic acid etc.). They may be sterilized, for example, by filtration through a bacteria-retaining filter, by incorporation of sterilizing agents in the compositions or by irradiation. They also may be manufactured in the form of sterile solid compositions, for example, by freeze-drying, and which can be dissolved in sterile water or some other sterile diluents for injection immediately before use.

Other compositions for administration include liquids for external use, and endermic liniments (ointment, etc.), suppositories and pessaries which comprise one or more of the active compound(s) and may be prepared by known methods.

MATERIALS AND METHODS

Cell Culture

Rat W256 cells (originally obtained from the Division of Cancer Treatment, NIH, Frederick, Md.) were maintained in minimum essential medium (MEM; Gibco Life Technologies, MD) supplemented with 5% fetal calf serum (FCS) and antibiotics. Cells were subcultured using 2 mM EDTA as previously described (Tang, D. G., et al., Int. J. Cancer 65:102–111 (1993a)). Rat aortic endothelial cells (RAEC; Tang, D. G., et al., Int. J. Cancer 65:102–111 (1993a)) and murine microvascular endothelial cells (CD clone 4; Tang, D. G., et al., Biochem. Biophys. Res. Commun. 211:462–468 (1995a)) were kindly provided by Dr. C. A. Diglio (Department of Pathology, Wayne State University, Detroit, Mich.) and maintained in DMEM (Gibco Life Technologies, MD) supplemented with 10% FCS (Gibco Life Technologies, MD) and antibiotics. Other cell lines including HUVEC (human umbilical vein endothelial cells), human erythroleukemia (HEL), rat MTLn-3 mammary adenocarcinoma cells were obtained from the American Type Culture Collection, Rockville, Md. and cultured according to the conditions recommended by the producers or as previously described (Tang, D. G., et al., J. Biol. Chem. 268:22883–22894 (1993b)).

Chemicals and Treatment

The following classes of chemicals were used in the present study. (1) General LOX inhibitors NDGA (Nordihydro guaiaretic acid), ETYA and ETI (5,8,11-eicosatriynoicacid; Biomol, Plymouth, Pa.). (2) General COX inhibitors indomethacin and ibuprofen (Biomol). (3) 12-LOX-selective inhibitors CDC (cinnamyl-3,4-dihydroxy-a-cyanocinnamate) and baicalein obtained from Biomol (Plymouth, Pa.). (4) 12-LOX-selective inhibitors represented by BHPP (N-benzyl-N-hydroxy-5-phenylpentanamide) (Liu, B., et al., Lab. Invest. 70:314–323 (1994); Chen, Y. Q., et al., Cancer Res. 54:1574–1579 (1994), compounds described in U.S. Pat. Nos. 5,292,884, and 5,238,832 as follows:

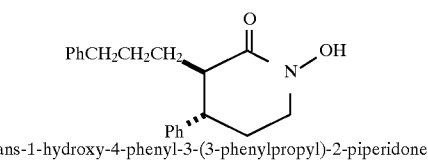

trans-1-hydroxy-4-phenyl-3-(3-phenylpropyl)-2-piperidone    214

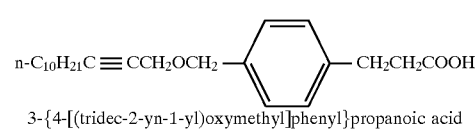

3-{4-[(tridec-2-yn-1-yl)oxymethyl]phenyl}propanoic acid    199

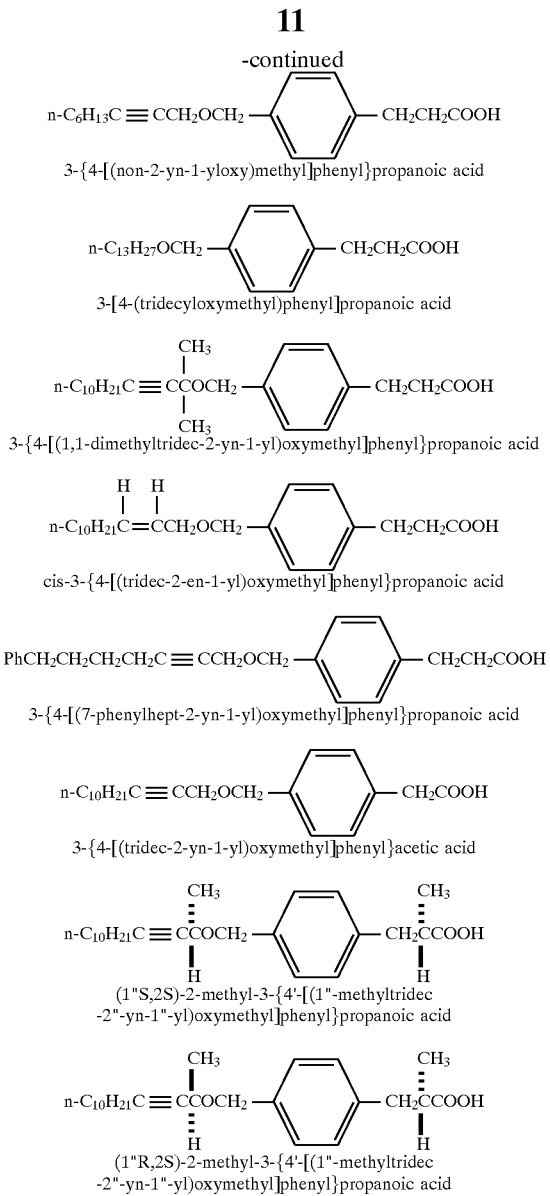

The compounds are cyclic hydroxamic acids (U.S. Pat. Nos. 5,234,933 and 5,292,884) of the formula:

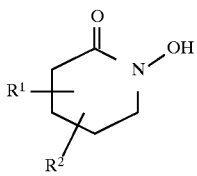

wherein $R^1$ is $C_1$ to $C_{24}$ alkyl and wherein $R^2$ is benzyl; and

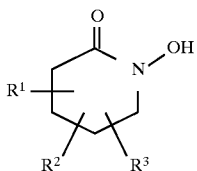

$R^1$, $R^2$ and $R^3$ each, independently, is hydrogen, C1–24 alkyl, C2–24 alkenyl or a group of the formula:

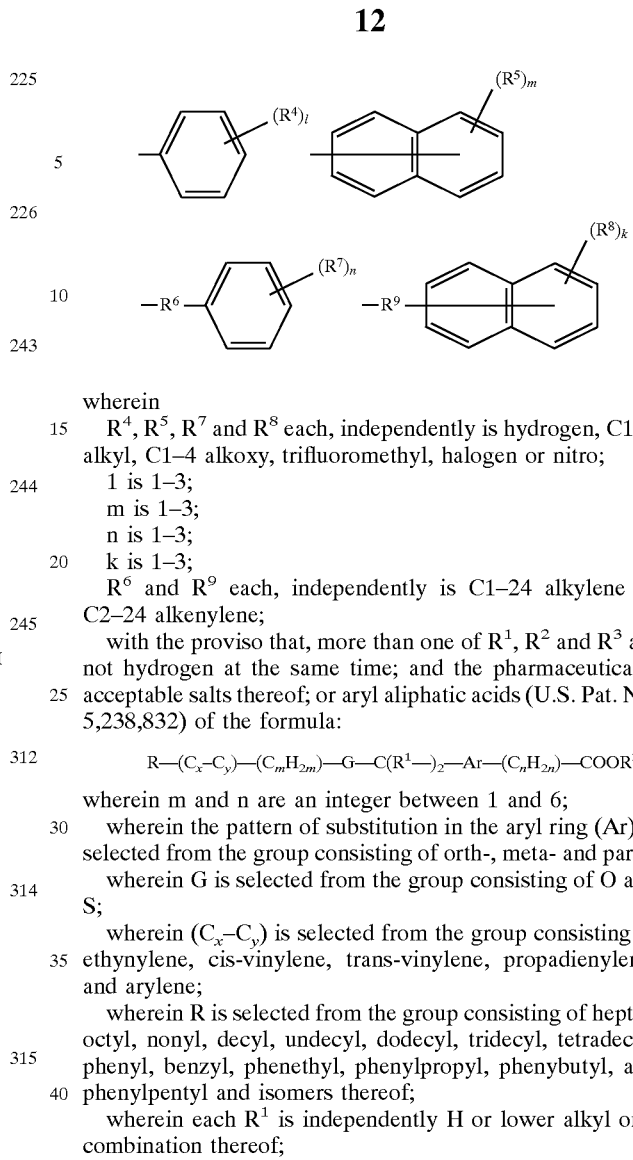

wherein
$R^4$, $R^5$, $R^7$ and $R^8$ each, independently is hydrogen, C1–4 alkyl, C1–4 alkoxy, trifluoromethyl, halogen or nitro;
l is 1–3;
m is 1–3;
n is 1–3;
k is 1–3;
$R^6$ and $R^9$ each, independently is C1–24 alkylene or C2–24 alkenylene;
with the proviso that, more than one of $R^1$, $R^2$ and $R^3$ are not hydrogen at the same time; and the pharmaceutically acceptable salts thereof; or aryl aliphatic acids (U.S. Pat. No. 5,238,832) of the formula:

$$R-(C_x-C_y)-(C_mH_{2m})-G-C(R^1-)_2-Ar-(C_nH_{2n})-COOR^2$$

wherein m and n are an integer between 1 and 6;
wherein the pattern of substitution in the aryl ring (Ar) is selected from the group consisting of orth-, meta- and para-,
wherein G is selected from the group consisting of O and S;
wherein $(C_x-C_y)$ is selected from the group consisting of ethynylene, cis-vinylene, trans-vinylene, propadienylene, and arylene;
wherein R is selected from the group consisting of heptyl, octyl, nonyl, decyl, undecyl, dodecyl, tridecyl, tetradecyl, phenyl, benzyl, phenethyl, phenylpropyl, phenylbutyl, and phenylpentyl and isomers thereof;
wherein each $R^1$ is independently H or lower alkyl or a combination thereof;
wherein $R^2$ is H, a salt, lower alkyl or aralkyl.

(5) Three selective 5-LOX inhibitors, caffeic acid, 5,6-dehydro-arachidonic acid, and AA-861 were purchased from Biomol. In general, these chemicals were used at 0.1–1,000 μM as specified in the Results. Most of these compounds were prepared in either ethanol or DMSO. Therefore, in all the controls throughout the study, either ethanol or DMSO was utilized, whose final concentrations in the culture media were always less than 0.1%. In all the cases the pretreatment and/or treatment was performed in normal culture media, i.e., MEM-5% FCS, unless otherwise indicated.

Antibodies and Immunoblotting

A rabbit polyclonal anti-12-LOX was purchased from Oxford Biomedical (Rochester, Mich.). Another rabbit polyclonal antibody against platelet-type 12-LOX was generated using the human 12-LOX-specific peptide (WTLKAGALEMALKRVYTL—SEQ ID NO: 1; corresponding to the amino acid 176–193 of human platelet 12-LOX). The peptide was synthesized using the Fmoc solid phase methods utilizing MAP resin technology (Research Genetics, Huntsville, Ala.). A rabbit was immunized with the peptides and bled 4, 8 and 10 weeks post immunization. The IgG fraction was purified from the antisera using a combination of ammonia sulfate precipitation and protein A resin.

Briefly, one volume of serum was mixed with an equal volume of 0.15M NaCl. Ammonium sulfate was then added and the mixture stirred for 2 hours. The precipitated proteins were centrifuged, resuspended in a small volume of 0.15M NaCl, and dialyzed against PBS. Afterwards, the sample was mixed with one volume of loading buffer (1.5M glycine, 3M NaCl, pH 8.9) and loaded onto a 5 ml protein A column. The column was washed with 20 ml of loading buffer and IgG was eluted with 100 mM citric acid (pH 7.4). The eluate was neutralized with 1M Tris-HCl (pH 7.4) and dialyzed against PBS. The IgG preparation was then aliquoted and stored at −20° C. until use. The anti-12-LOX IgG purified from the 10 week rabbit antisera was used in the present study.

The above antibodies were used in Western blotting. Whole cell lysates were prepared from cultured W256 cells or rat platelets using the TNC lysis buffer as previously described (Tang, D. G., et al., J. Biol. Chem., 268:22883–22894 (1993b)). The primary antibody concentration was 1 mg/ml and the goat anti-rabbit IgG conjugated to horseradish peroxidase was used at 1:1,000 dilution. The molecular weight markers were bought from either Sigma (St. Louis, Mo.) or Bio-Rad (Richmond, Calif.). The ECL Western blotting detection kit was obtained from Amersham (Arlington, Ill.).

Northern Blotting, RNase Protection Assays, PCR and RT-PCR

The basic protocol was as described previously (Tang, D. G., et al., J. Biol. Chem., 268:22883–22894 (1993b); Tang, D. G., et al., Int. J. Cancer 60:418–425 (1995d)). Total cellular RNA was prepared from cultured W256 cells or MTLn-3 mammary adenocarcinoma cells with acid guanidinium thiocyanate-phenol-chloroform extraction method (Chomczynski, BioTechnique, 15:532–537 (1993)) using the TRI-REAGENT kit (MRC, Inc., Cincinnati, Ohio). Poly(A$^+$) RNA was isolated using POLYATRACT RNA kit (Promega, Wis.). Either 25 mg of total RNA (for MTLn-3 cells) or 5 mg of mRNA (for W256 cells) was separated on a 1% formaldehyde/agarose gel and transferred to the nylon membrane, which was probed with a full-length $^{32}$P-labeled 12-LOX cDNA (kindly provided by Dr. C. Funk, University of Pennsylvania). Prehybridization, hybridization, post-hybridization wash (high stringency), and autoradiography were performed as previously described (Tang, D. G., et al., J. Biol. Chem., 268:22883–22894 (1993b); Tang, D. G., et al., Int. J. Cancer 60:418–425 (1995d)). RT-PCR was performed basically as previously described (Chen, Y. Q., et al., Cancer Res. 54:1574–1579 (1994)) using human sequence-based 12-LOX primers. For ribonuclease protection assays (RPA), a PCR method was used to generate a riboprobe template that covers the 12-LOX cDNA region sharing the lowest homology with other LOX such as 15-LOX. Specifically, a modified T7 RNA polymerase promoter (5'-GGATCCTAATACGACTCACTATAGGGAGG-3'—SEQ ID NO:2) was appended to the 5'-end of the sense PCR primer (5'-CTGGACTTTGAATGGACA-3'—SEQ ID NO:3; corresponding to the nucleotide 514–531 of the human 12-LOX cDNA; Funk, C. D., et al., Proc. Natl. Acad. Sci. USA 87:5638–5642 (1990)). Similarly, a modified SP6 RNA polymerase promoter (5'-CTCGAGCTATTCTATAGT-GTCACCTAAAT-3'—SEQ ID NO:4) was appended the 5'-end of the antisense PCR primer (5'-CTCAGGAGGGTGTAAACA-3'—SEQ ID NO:5; corresponding to nucleotide 567–584 of the human 12-LOX cDNA; Funk et al., Proc. Natl. Acad. Sci., USA 87:5638–5642 (1990)). These primers were synthesized on a Gene Assembler Plus (Pharmacia LKB) and purified by repeated phenol-chloroform extraction and ChromaSpin 10 column size exclusion chromatography (Clontech, Calif.). The quality and sizes of the synthesized oligos were examined by running 1 mg on a 20% denaturing urea/polyacrylamide gel. Purified primers at equimolar concentrations were utilized in PCR amplifications, using 100 ng of 12-LOX cDNA (Funk et al., Proc. Natl. Acad. Sci. USA 87:5638–5642 (1990)) as the template. The PCR was performed on a GeneAmp 9600 thermocycler (Perkin-Elmer, Calif.) at 94° C.×30 sec., 50° C.×30 sec., and 72° C.×1 min. for a total of 30 cycles. The PCR products were separated on a 5% urea/polyacrylamide gel and the single band of the expected size (~75 bp) was cut out and purified. The in vitro transcription and riboprobe generation were performed as previously described (Tang, D. G., et al., Int. J. Cancer 60:418–425 (1995d)). Briefly, the sense and antisense riboprobes were synthesized with T7 and SP6 RNA polymerases, respectively, by including ($\alpha$-$^{32}$P)-UTP in the transcription mixture containing 500 mM each of ATP, GTP, and CTP, 3.125 mM of [$\alpha$-$^{32}$P] UTP (800 Ci/mmol), and 5 mM of the cold UTP. The transcription reaction (in a total of 20 µl) was initiated by adding 1 µl (10 U) of RNA polymerase and performed by incubating the mixture at 25° C. for 1 hour. At the end of the reaction, the DNA templates were degraded with RNase-free DNase and the run-off transcripts were purified with the Chroma-spin size-exclusion chromatography (Clontech). The quality of the transcribed riboprobes was evaluated by running 0.5 µg of the purified products on a 3% formaldehyde/MOPS LMP (Low melting point) agarose gel followed by autoradiography. In all cases, single-band species of the expected size were identified for both the sense and antisense riboprobes (data not shown). Hybridization (using 20 µg total RNA) and nuclease digestion were performed using a RPA II ribonuclease protection kit (Ambion, Austin, Tex.) as previously described (Tang, D. G., et al., Int. J. Cancer 60:418–425 (1995d)). The protected band was revealed by performing autoradiography.

Characterization of Apoptosis By Light Microscopy

Cells cultured in 96-well plates or T25 culture flasks were treated with various chemicals. Cellular morphology was observed using a Nikon Diaphot (Mager Scientific, Inc., Dexter, Mich.) inverted microscope. Photomicrographs were taken using Tmax 400 (Rochester, Mich.) black and white films. Apoptotic cells were determined on the basis of their typical morphology, i.e., shrunken cell body, membrane blebbing, and appearance of apoptotic bodies.

Characterization of Apoptosis By Electron Microscopy

Cells cultured in 96-well plates or T25 culture flasks were treated with various chemical compounds. At the end of treatment, cells were fixed in 1.25% glutaraldehyde-1% paraformaldehyde mixture in 0.1M sodium cacodylate. Following fixation, samples were sequentially treated, finally dehydrated in Freon TF-113, and critical point dried by Freon 13 in a Bomar critical point drying apparatus. Finally, samples were examined and photographed on a Phillips 201 transmission electron microscope operating at accelerating voltages of either 80 or 100 kV.

DNA Fragmentation and Quantification $5\times10^6$ cells cultured in T75 flasks were treated with NDGA or other chemicals. Subsequently, cells were harvested and fragmented DNA extracted with 200 µl of the lysis buffer (50 mM Tris-HCl, pH 7.4, 40 mM EDTA, 1% NP-40) for 2 minutes. Samples were then centrifuged at 500 g for 5 minutes. The resultant supernatants were transferred to a clean set of eppendorf tubes and the pellets redissolved in 200 µl lysis buffer and extracted for 2 minutes. Samples were centrifuged again and the resultant supernatants combined with previous supernatants. Subsequently, SDS and DNase-free RNase were added to the pooled supernatants to the final concentrations of 0.1% and 5 $\mu g/\mu l$, respectively, and samples incubated at 37° C. for 1.5 hours. At the end of RNase treatment, proteinase K (2.5 $\mu g/\mu l$ final concentration) was added and samples further incubated for 2 hours at 50° C. Samples were then extracted once with alkaline phenol/chloroform/isoamyl alcohol (25:24:1) and DNA precipitated with 0.3M NaAc (pH 5.2). DNA from equal number of cells or equal amounts of DNA (generally 20 mg) was run on a 1.2% agarose gel and the DNA ladder formation visualized by ethidium bromide staining. To quantitate DNA fragmentation, W256 cells were either labeled for 16 hours or briefly pulsed (2 hours) with 1 mCi/ml ($^3$H)-thymidine and then fragmented DNA as well as intact genomic DNA isolated as above. The amount of DNA was measured on a scintillation counter and the results expressed as the % fragmentation. Alternatively, DNA fragmentation was quantitated using the Cell Death Detection ELISA kit from Boehringer Mannheim (Indianapolis, Ind.). This kit measures the mononucleosomes and oligonucleosomes released into the cytoplasm of apoptotic cell population using a specific monoclonal antibody recognizing only the histone-associated DNA (e.g., nucleosomes).

Quantification of Apoptosis By Flow Cytometric Analysis

2–5×10$^6$ cells cultured in T75 culture flasks were treated with different doses of NDGA or other chemicals. At the end, cells were harvested with 2 mM EDTA and washed once with cold PBS containing 5 mM EDTA. Subsequently, cells were resuspended in 1 ml cold PBS/5 mM EDTA and 1 ml of cold absolute ethanol was added to fix cells (30 min, room temperature). At the end of fixation, cells were pelleted and resuspended in 0.5 ml of PBS/5 mM EDTA, to which 20 $\mu l$ RNase A/T1 (1 mg/ml: Ambion, Austin, Tex.) was added. Cells were incubated for 30 minutes at room temperature (to allow the soluble fragments to leak out of the cells), after which 0.5 ml 100 $\mu g/ml$ PI (propidium iodide, in PBS) was added and mixed. The samples are stored at 4° C. until analyzed later on an Epics II flow cytometer (Coulter, Fla.).

Results and Discussion

W256 Cells Express Platelet-Type 12-LOX

Figure 1B:
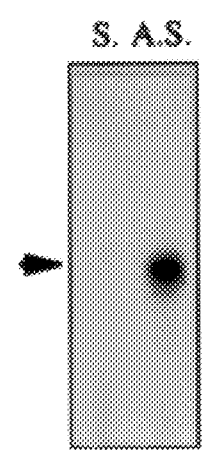
Figure 1C:
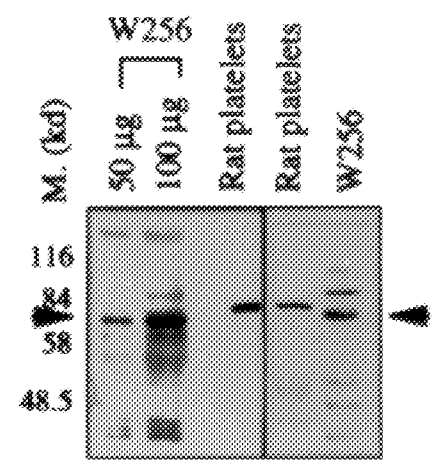

W256 cells, originally isolated from a spontaneous tumor in the mammary gland of a pregnant albino rat, have recently been characterized to be of monocytoid origin (Simpkins, H., et al., Cancer Res. 51:1334–1338 (1991)). These cells proliferate very fast and, like most leukemia and lymphoma cells, have a short population doubling time (12–16 hours). Our previous work utilizing RT-PCR demonstrated the presence of platelet-type 12-LOX in W256 cells. We confirmed this conclusion in this study using several different molecular approaches. Northern blotting under high stringency-conditions with full-length 12-LOX cDNA probe (Funk, C. D., et al., Proc. Natl. Acad. Sci. USA 87:5638–5642 (1990a)) detected a single ~3.2 kb band in W256 cells (FIG. 1A). To exclude the possibility of cross reaction between the 12-LOX cDNA probe and other mammalian LOXs, i.e., 5- and 15-LOX, we generated PCR primers that cover the region (nucleotide 514 to 584) of 12-LOX that shares the lowest homology with other LOXs. Modified T7 and SP6 RNA polymerase promoter sequences were appended to the 5'- ends of the sense and antisense primers, respectively, so that the amplified PCR fragment could be directly used in generating the corresponding sense and antisense riboprobes. As shown in FIG. 1B, the antisense riboprobe protected an expected band of ~75 bp while the sense probe did not detect any specific band suggesting that this region between the human and rat 12-LOXs is very similar, if not identical. Western blotting (FIG. 1C, left panel) with a rabbit polyclonal anti-12-LOX antibody revealed a major ~72 kd protein which was slightly smaller in M.W. than the rat platelet 12-LOX (~74 kd). An anti-peptide antibody against 12-LOX also revealed the same reaction pattern (FIG. 1C, right panel). The reactivity of these two antibodies towards the 72 kd 12-LOX band could be blocked by preincubating the antibodies with platelet membrane preparations (data not shown). W256 cells appear to express very little or no 5- and 15-LOX since Northern blotting with 5 $\mu g$ mRNA using human 15-LOX (kindly provided by Dr. E. Sigal, Syntex, Palo Alto, Calif.), or human (Oxford, Mich.) or rat (courtesy of Dr. S. Crooke, ISIS Pharmaceuticals, Carlsbad, Calif.; Balcarek, J. M., et al., J. Biol. Chem. 263:13937–13941 (1988)) 5-LOX cDNA probes did not detect any specific band(s) (data not shown). These observations overall are consistent with the recent observations that human monocytes constitutively express high levels of 12-LOX with low level expression of 5-LOX and no detectable expression of 15-LOX (Kaminski, W. E., et al., Blood 87:331–340 (1996)).

12-LOX is a Critical Survival Factor For W256 Cells

Figure 2A:
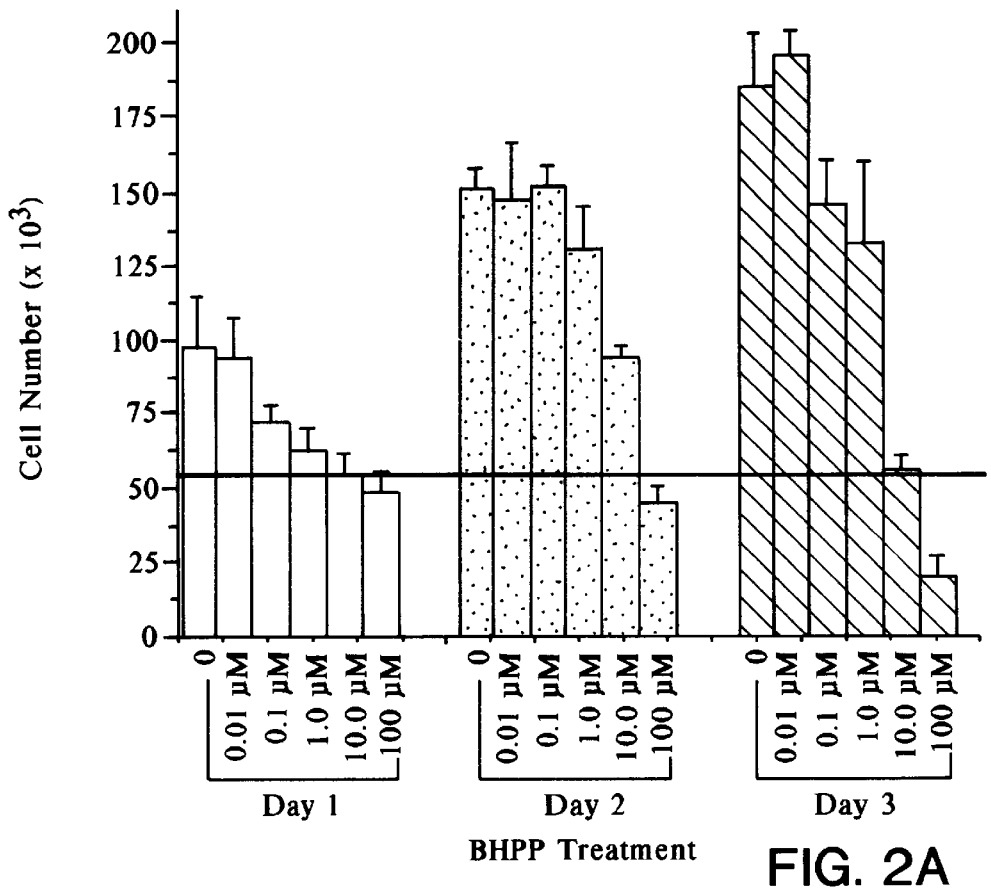
FIGS. 2A, 2B and 2C show that 12-LOX is a critical survival factor for tumor cells as revealed by induction of W256 cell apoptosis by LOX but not COX inhibitors.
Figure 2F:
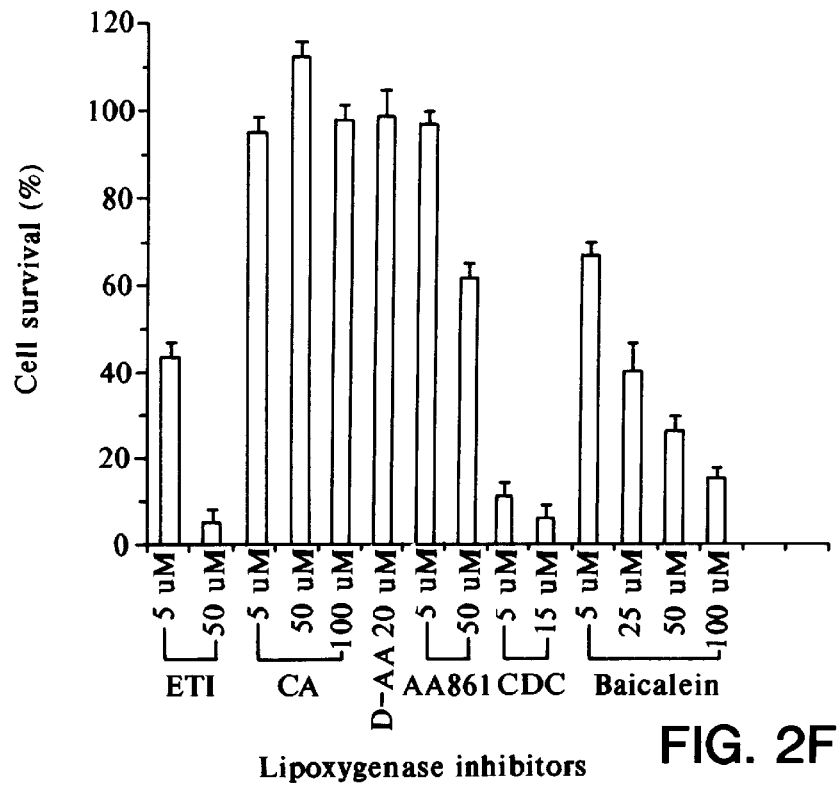
FIG. 2F is a graph showing quantitation of W256 cell apoptosis induced by LOX inhibitors. The surviving cells were quantitated as described in reference to FIG. 2A. The treatment was for 24 hours and the results represent mean±S.E. derived from three independent experiments. CA, caffeic acid; D-AA, 5,6-dehydro-arachidonic acid.
Figure 2B:
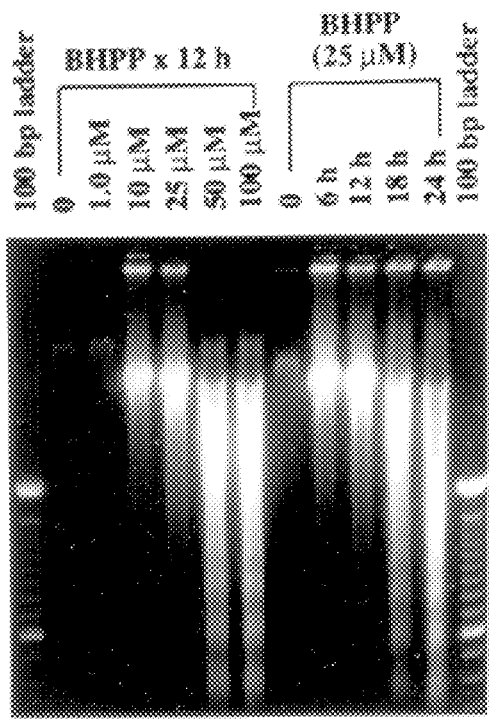
Figure 2C:
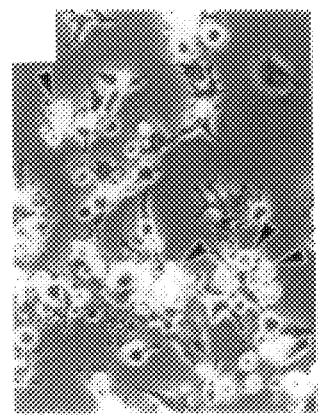
Figure 2D:
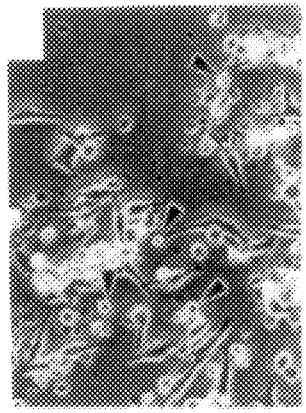
Figure 2E:
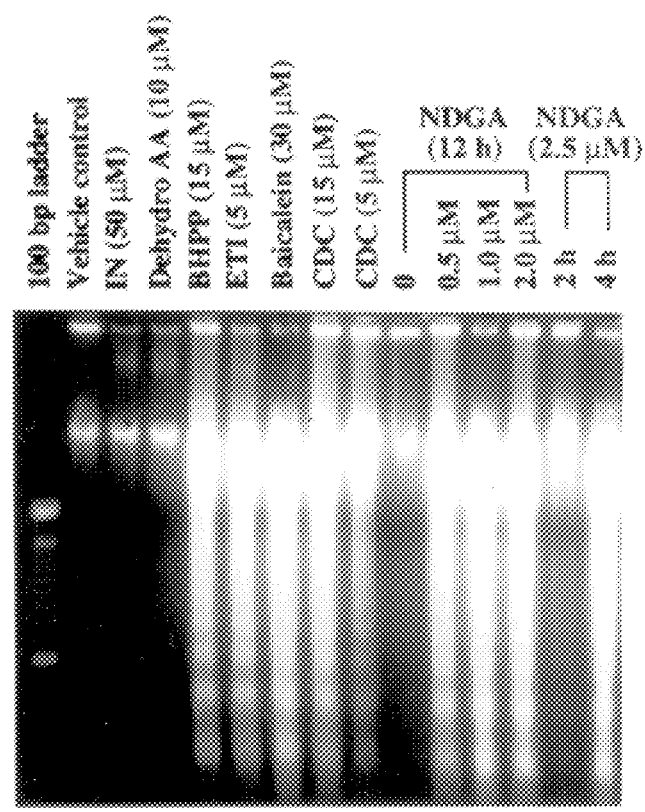
FIG. 2E is a photograph of a gel showing DNA fragmentation induced by various LOX inhibitors. W256 cells were treated with NDGA or other inhibitors (at indicated doses; 24 hours) in serum-containing MEM and fragmented DNA prepared as described above. IN, indomethacin; Dehydro-AA, 5,6-dehydro-arachidonic acid.

From above, it can be seen that serum-cultured W256 cells express high levels of endogenous 12-LOX mRNA and protein. We hypothesize that this basal level expression of 12-LOX may not only be important for the growth of W256 cells, it may also be critical for the cell survival. This hypothesis was tested using a panel of general or selective LOX inhibitors. BHPP compound has been shown to preferentially inhibit the 12-LOX activity (Liu, B., et al., Lab. Invest. 70:314–323 (1994); Chen, Y. Q., et al., Cancer REs. 54:1574–1579 (1994)), demonstrated a dose-dependent inhibitory effect on W256 cell growth (FIG. 2A). The DNA fragmentation was observed with 10 $\mu M$ BHPP treatment (12 hours) and the inhibitor revealed a dose- and time-dependent effect (FIG. 2B). NDGA, a general LOX inhibitor, demonstrated the most potent apoptosis-inducing effect. It induced apoptosis at 0.1 $\mu M$ 24 hours post drug application. Two hours after 2.5 $\mu M$ NDGA treatment, numerous apoptotic cells with typical membrane blebbing could easily be seen (FIG. 2C; arrowheads). At 4 hours, the majority of cells in culture were dead and released membrane-bound apoptotic bodies (FIG. 2D; arrowheads). DNA fragmentation assays revealed a similar time- and dose-dependent relationship (FIG. 2E). NDGA-induced apoptosis declined at $\geq 10$ $\mu M$. At 25 $\mu M$, a mixed apoptosis and necrosis was observed, while at $\geq 50$ $\mu M$, NDGA induced a rapid necrotic response which affected the whole cell population. Another general LOX inhibitor, ETI (5, 8, 11-eicosatriynoic acid; Hammarstrom, S., Biochem. Biophys. Acta 487:517–519 (1977)) also induced potent cell death, with obvious effects observed at 5 $\mu M$ (FIG. 2F). Of the three selective 5-LOX inhibitors tested, caffeic acid (Koshihara, Y., et al., Biochim. Biophys. Acta 792:92–97 (1984)) and 5, 6-dehydro-arachidonic acid (Sok, D. E., et al., Biochem. Biophys. Res. Commun. 107:101–108 (1982)) did not induce apoptosis at the doses tested (5–100 $\mu M$ and 1–50 $\mu M$, respectively; FIGS. 2E and 2F and data not shown). Another select and potent 5-LOX inhibitor, AA-861 (Yoshimoto, Y., et al., Biochim. Biophys. Acta 713:470–473 (1982)) induced W256 cell apoptosis only at $\geq 20$ $\mu M$. It is not known whether this effect of AA-861 resulted from a specific inhibition of 5-LOX or from inhibition of other LOXs. In addition to BHPP, two other selective 12-LOX inhibitors, baicalein (5, 6, 7-trihydroxyflavone; Sekaya, I. and H. Okuda, Biochem. Biophys. Res. Commun. 105:1090–1095 (1982)) and CDC (Cho, H., et al., J. Med.

Chem. 34:1503–1505 (1991)), also induced dose-dependent DNA fragmentation and apoptosis of W256 cells (FIGS. 2E and 2F). In contrast to the results obtained with LOX inhibitors, two COX inhibitors, indomethacin (preferentially inhibiting COX-1 over COX-2) and ibuprofen (with comparable inhibition for both COX-1 and COX-2) did not induce cell death at the doses tested (5–100 $\mu$M) (FIG. 2E and data not shown). W256 cell apoptosis induced by NDGA and other LOX inhibitors were confirmed and studied in detail by electron microscopy. As early as 15 minutes post NDGA treatment, condensed cytoplasm, increased cytoplasmic vacuoles, and reduced plasma membrane microvilli were observed. By 30 minutes, membrane blebbings, large cytoplasmic spacings due to plasma membrane invagination, and condensed nuclear chromatin were observed. By this time, the size and morphology of most cytoplasmic organelles (e.g., mitochondria and ER) appeared to be normal. By 1 hour, with all the above-described alterations worsening, the most prominent changes were the appearance of numerous swollen mitochondria. By 2 hours, apoptosis became full-blown and affected the majority of the cell population and membrane-bound apoptotic bodies were prevalent (data not shown). Flow cytometric analysis also confirmed NDGA-induced apoptosis.

12-LOX May Also Serve as a Critical Survival Factor For Other Tumor Cells

Figures 1, 4A:
FIGS. 4A-1 to 4A-3, 4B-1 to 4B-3, 4C-1 to 4C-3 and 4D-1 to 4D-3 are photographs of cells treated with various compounds which induce apoptotic death of W256 carcinosarcoma cells.
Figures 2, 4A:
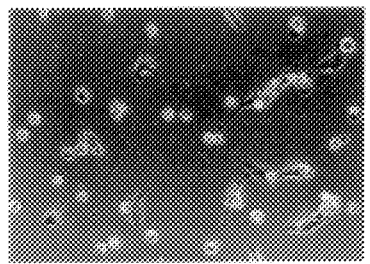
Figures 3, 4A:
Figures 1, 4B:
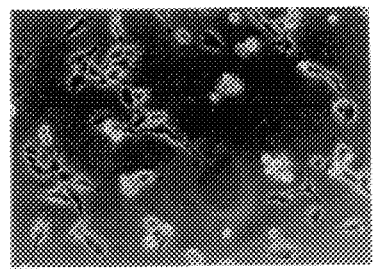
Figures 2, 4B:
Figures 3, 4B:
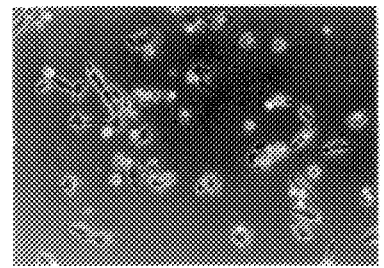
Figures 1, 4C:
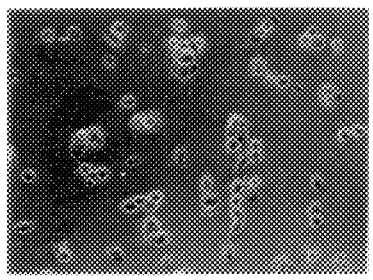
Figures 2, 4C:
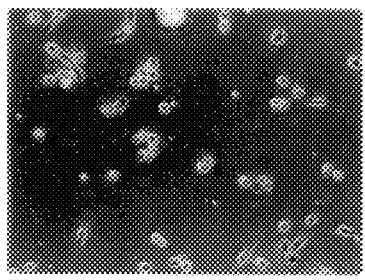
Figures 3, 4C:
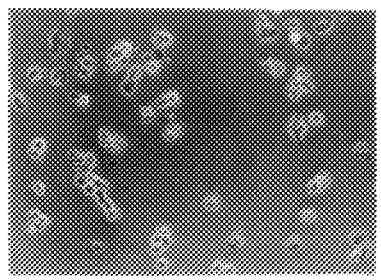
Figures 1, 4D:
Figures 2, 4D:
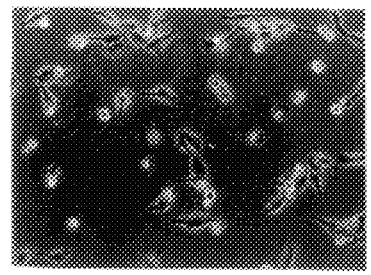
Figures 3, 4D:

The above results suggest that 12-LOX is a critical survival factor for W256 carcinosarcoma cells. Inhibition/blocking of 12-LOX activity with either general or selective inhibitors will trigger the apoptotic cell death. To determine whether NDGA-induced apoptosis is unique to W256 cells, the effect of NDGA was screened on several cultured normal and tumor cells derived from human, rat, and mouse. As shown in FIG. 3A, NDGA also induced apoptosis of some tumor cells other than W256 cells. MTLn-3, a rat mammary adenocarcinoma cell line which expressed 12-LOX (FIG. 3A, left panel), showed high spontaneous apoptosis, which was further enhanced by NDGA as well as by 12-LOX-selective inhibitors BHPP, and, much less dramatically, CDC and baicalein (FIG. 3A, right panel). COX inhibitor, indomethacin (IN), was ineffective at 50 $\mu$M (FIG. 3A, right panel) or 200 $\mu$M (not shown). Rat basophilic leukemia (RBL-1) cells have been known to express 5-LOX (Balcarek, J. M., et al., J. Biol. Chem. 263:13937–13941 (1988)). Whether they also express 12- and/or 15-LOX is unknown. Treatment of REL-1 cells with NDGA at $\geq$25 $\mu$M of NDGA induced apoptosis (FIG. 3B). On the other hand, treatment of cells with 5-LOX inhibitors AA-861, caffeic acid, or 5,6-dehydro-arachidonic acid at up to 100 $\mu$M did not induce apoptotic cell death (data not shown), suggesting that NDGA-induced RBL-1 apoptosis may be mediated by its effects on 12- and/or 15-LOX but not 5-LOX. HEL (human erythroleukemia) cells express 12-LOX (Funk, C. D., et al., Proc. Natl. Acad. Sci., USA 87:5638–5642 (1990)) and, most probably, also express other LOXs. At $\geq$25 $\mu$M, NDGA also induced apoptosis of HEL cells (FIGS. 3C–3E). In contrast, NDGA, BHPP or a 12-LOX-specific antisense oligonucleotide (5'-CTCAGGAGGGTGTAAACA-3'— SEQ ID NO:6) did not induce apoptosis of rat aortic endothelial cells (RAEC) although they caused strong death of W256 cells (FIG. 3F). Human umbilical vein and mouse pulmonary capillary (Tang, D. G., et al., Int. J. Cancer 60:418–425 (1995d)) endothelial cells also did not respond to NDGA (data not shown) although it is known that endothelial cells possess various LOX activities (Spector, A. A., et al., Prog. Lipid Res. 27:271–323 (1988); Rosolowsky, M., and W. B. Campbell, Biochem. Biophys. Acta 1299:267–277 (1996)).

The Tested Compounds (i.e., 12-LOX Inhibitors; U.S. Pat. No. 5,292,884; U.S. Pat. No. 5,238,832) Induce Apoptosis of W256 Cells The preceding work suggested that in many tumor cells but normal cells, 12-LOX expression and function/activity are essential survival factors, without which tumor cells will undergo a suicidal death through apoptosis. These experimental findings suggest that induction of tumor cell apoptosis by targeting to inhibition for the 12-LOX function/activity is a novel mechanism-based avenue in searching for anti-cancer drugs. U.S. Pat. No. 5,292,884, U.S. Pat. No. 5,238,832, and U.S. Pat. No. 5,234,933 describe compounds which have varying degrees of inhibitory activity towards 12-LOX. Based on the preceding presentations, some of these 12-LOX-targeted compounds also induce tumor cell apoptosis. BHPP, induced strong and potent apoptosis of W256 cells. Ten compounds were chosen (referred to as compound 199, 214, 225, 226, 243, 244, 245, 312, 314 and 315 thereafter) for the assays. The screening was performed with W256 cells using a series of concentrations (0.1 to 100 $\mu$M) of these compounds and followed a time course up to 40 hours. NDGA, BHPP and baicalein were used as positive controls. The results were summarized in the accompanying Table.

TABLE 1

W256 Cell Apoptosis Induced by Selected Compounds (Light Microscopy)

| Compound | 3–4 h | ~18 h | 24 h | 40 h |
|---|---|---|---|---|
| NDGA | | | | |
| 0.1 $\mu$M | | | ++ apop | >95% a. |
| 1 $\mu$M | | ++ apop | +++ apop | |
| 10 $\mu$M | apop./necro | apop/necro | 100% death | |
| 50 $\mu$M | 100% necro | | | |
| 100 $\mu$M | 100% necro | | | |
| BHPP | | | | |
| 0.1 $\mu$M | | | | |
| 1 $\mu$M | | | | |
| 10 $\mu$M | | | ++ apop | +++ |
| 50 $\mu$M | | +++ apop | +++ apop | >95% a. |
| 100 $\mu$M | Shape change | 100% necro | | |
| Baicalein | | | | |
| 0.1 $\mu$M | | | | |
| 1 $\mu$M | | | | |
| 10 $\mu$M | | ++ apop | ++ | +++ |
| 50 $\mu$M | | +++ apop | +++ | >95% a. |
| 100 $\mu$M | >95% a/n | | | |
| 199 | | | | |
| 0.1 $\mu$M | | | | |
| 1 $\mu$M | | | | |
| 10 $\mu$M | | + apop | ++ apop | ++ |
| 50 $\mu$M | | ++ apop | +++ apop | +++ |
| 100 $\mu$M | | >95% apop | | |
| 214 | | | | |
| 0.1 $\mu$M | | | | |
| 1 $\mu$M | | | | |
| 10 $\mu$M | | ++ apop | +++ | >90% a. |
| 50 $\mu$M | | +++ apop | +++ | >99% a. |
| 100 $\mu$M | | >95% apop | | |
| 225 | | | | |
| 0.1 $\mu$M | | | | |
| 1 $\mu$M | | | | |

TABLE 1-continued

W256 Cell Apoptosis Induced by
Selected Compounds (Light Microscopy)

| Compound | 3–4 h | ~18 h | 24 h | 40 h |
|---|---|---|---|---|
| 10 μM |  |  |  |  |
| 50 μM |  | ++ a/n | ++ a/n | +++ (n > a) |
| 100 μM | Rounding | >99% (a > n) |  |  |
| 226 |  |  |  |  |
| 0.1 μM |  |  |  |  |
| 1 μM |  |  |  |  |
| 10 μM |  |  | + apop | + apop |
| 50 μM |  | +++ apop | >75% n > a | >95% |
| 100 μM | Insoluble |  |  | n > a |
| 243 |  |  |  |  |
| 0.1 μM |  |  |  |  |
| 1 μM |  | + apop | + | ++ |
| 10 μM |  | ++ apop | ++ | +++ apop |
| 50 μM | +++ apop | 100% apop | 100% a |  |
| 100 μM | >90% apop |  |  |  |
| 244 |  |  |  |  |
| 0.1 μM |  |  |  |  |
| 1 μM |  |  | + apop | ++ apop |
| 10 μM |  | ++ apop | +++ | +++ |
| 50 μM | ++ apop | 100% a/n |  |  |
| 100 μM | Insoluble |  |  |  |
| 245 |  |  |  |  |
| 0.1 μM |  |  |  |  |
| 1 μM |  |  |  | ++ |
| 10 μM |  |  | ++ | ++ |
| 50 μM | ++ a/n | +++ a/n | 100% a/n |  |
| 100 μM | 100% a/n | 100% n > a |  |  |
| 312 |  |  |  |  |
| 0.1 μM |  |  |  |  |
| 1 μM |  |  | + apop | ++ |
| 10 μM |  | ++ apop | ++ | +++ |
| 50 μM |  | +++ a/n | 100% a/n |  |
| 100 μM | 100% necrosis |  |  |  |
| 314 |  |  |  |  |
| 0.1 μM |  |  |  |  |
| 1 μM |  |  |  |  |
| 10 μM | +++ apop |  | 100% apop |  |
| 50 μM | 100% death |  |  |  |
| 100 μM |  |  |  |  |
| 315 |  |  |  |  |
| 0.1 μM |  |  |  |  |
| 1 μM |  |  |  |  |
| 10 μM | >95% apop |  | 100% apop |  |
| 50 μM | 100% death |  |  |  |
| 100 μM |  |  |  |  |

*6 × 10⁴ W256 cells were plated into 24-well plates and cultured for 6 hours before adding drugs in fresh MEM-5% FCS (2 ml/well). The cell death was monitored under inverted phase microscope. Photomicrographs were taken at various time points. +, <25% population; ++, 25–50% population; +++, 50–75% of the population. apop. or a = apoptosis; necro or n = necrosis.

Figure 5A:
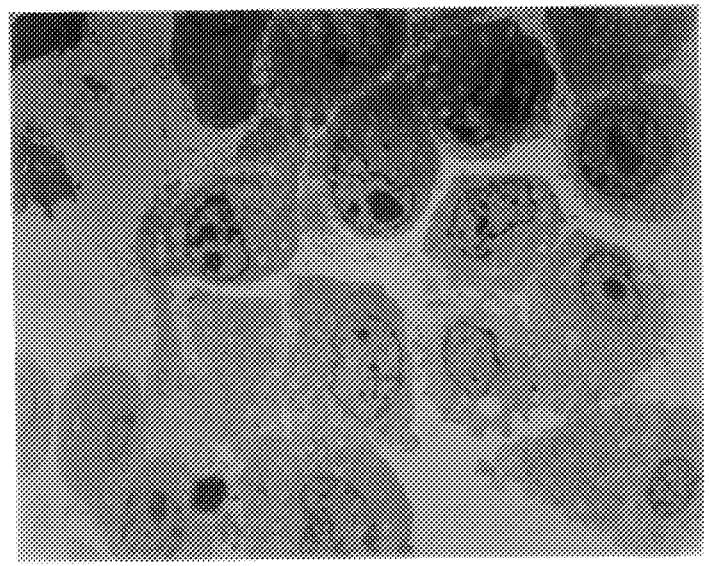
FIGS. 5A and 5B are photographs of cells showing examples of W256 cell apoptosis induced by compound 245.
Figure 5B:
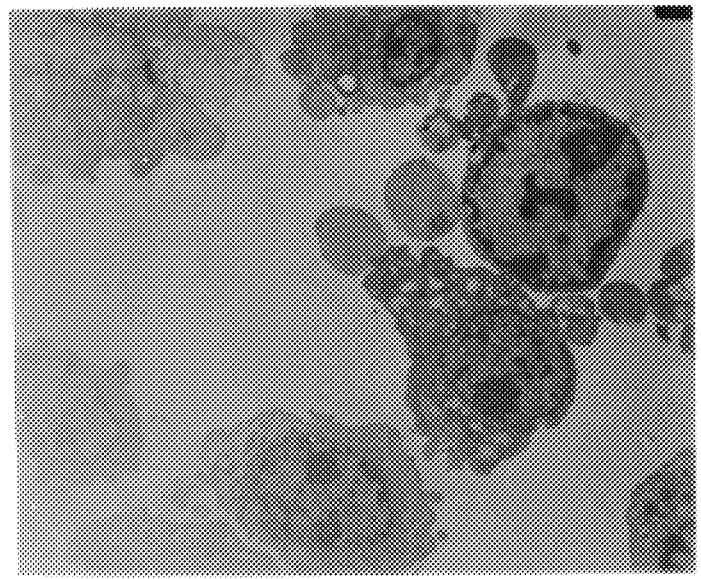
Figure 6A:
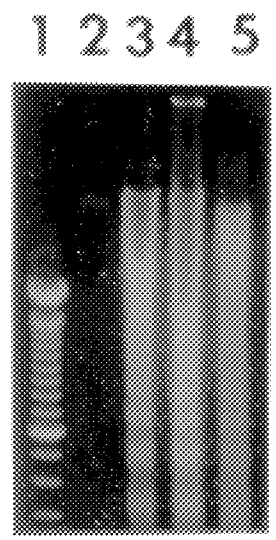
FIGS. 6A and 6B show the results with various compounds which induce DNA fragmentation of W256 cells.
Figure 6B:
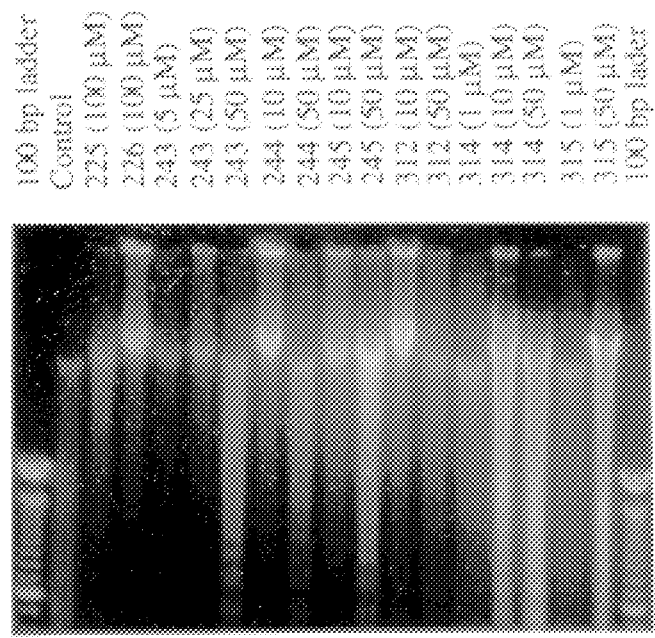
Figure 7A:
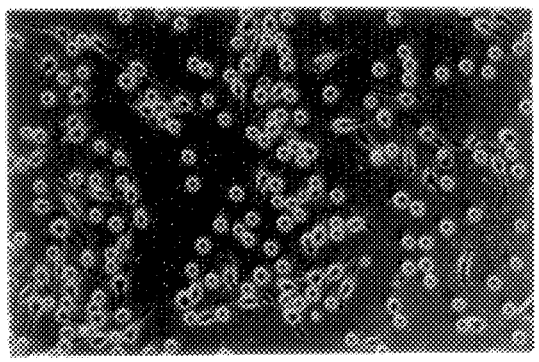
FIGS. 7A to 7D are photographs of cells showing how various compounds also induce apoptotic death of RBL-1 (rat basophilic leukemia) cells. Shown here are examples of photomicrographs of RBL-1 cells treated with compounds 199 and 214 as indicated. Original magnification, x200.
Figure 7B:
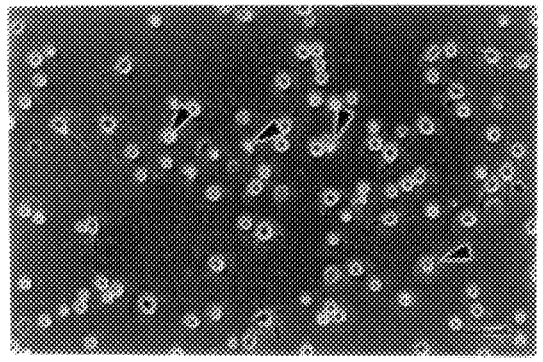
Figure 7C:
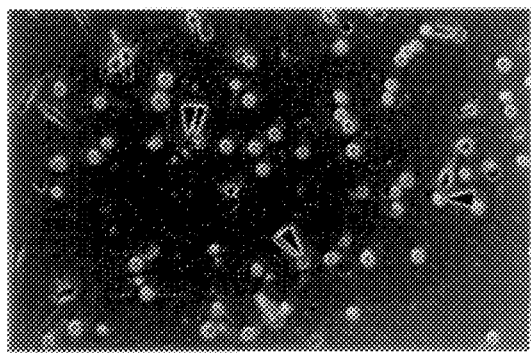
Figure 7D:
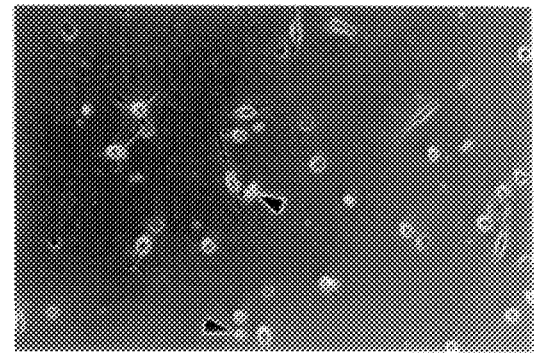

As revealed by light microscopy 4A-1 to 4A-3, 4B-1 to 4B-3, 4C-1 to 4C-3 and 4D-1 to 4D-3, electron microscopy (FIGS. 5A and 5B) as well as DNA fragmentation ladder assays (FIGS. 6A and 6B), all of these compounds demonstrate varying degrees of apoptosis-inducing effects. Compounds 314 and 315 demonstrated the most potent effects in inducing W256 cell death, followed by compounds 243, 244, 245, 199 and 214 which demonstrated very similar degree of death-inducing effects. The other three compounds showed lower efficacies (FIGS. 4A-1 to 4A-3, 4B-1 to 4B-3, 4C-1 to 4C-3 and 4D-1 to 4D-3 and FIGS. 6A and 6B as well as Table 1). The apoptotic nature of cell death induced by the tested compounds were confirmed by the electron microscopy studies as well as the ladder formation assays.

Figure 8A:
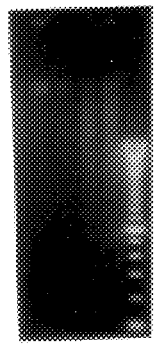
FIGS. 8A to 8F are photographs showing how various compounds induce apoptotic death of human tumor cells but not normal human endothelial cells.
Figure 8B:
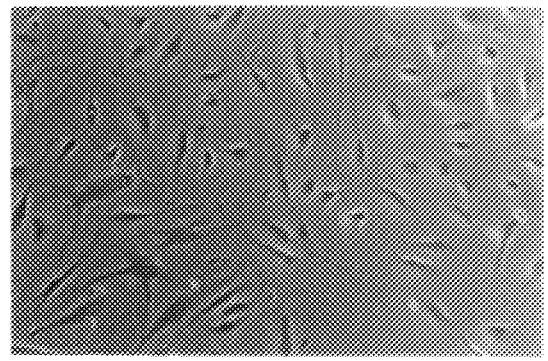
Figure 8C:
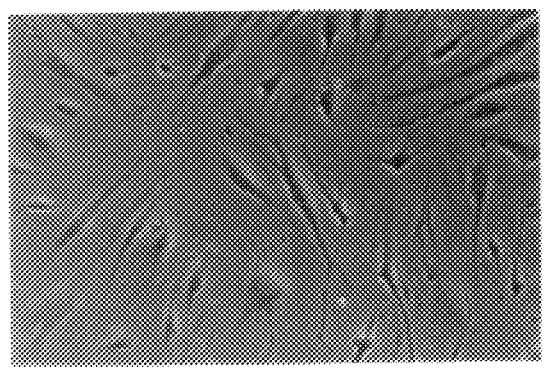
Figure 8D:
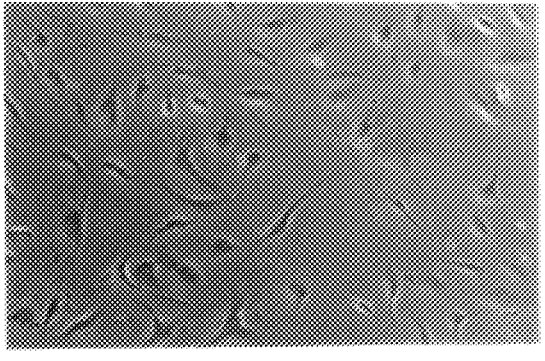
Figure 8E:
Figure 8F:
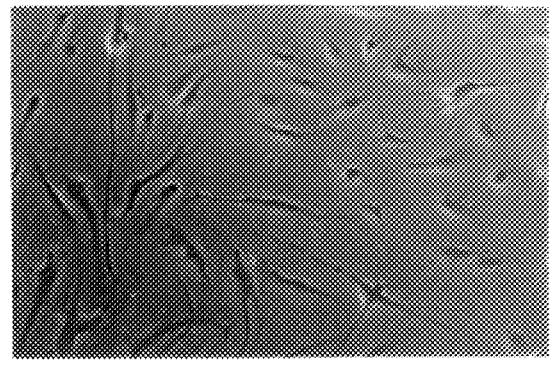

The Tested Compounds Also Induce Apoptosis of Other Tumor Cells Including Human Solid Tumor Cells But Not Normal Endothelial Cells Similar to the NDGA studies, the effects of the compounds was examined on some other rodent and human tumor cells. All the ten compounds tested (see above) induced apoptotic death of RBL-1 (rat basophilic leukemia) cells as exemplified in FIGS. 7A to 7D. Like NDGA, these compounds also induced apoptosis of human erythroleukemia (HEL) cells (data not shown). The effects of some of these compounds on human solid tumor was examined, specifically, A431 epidermoid carcinoma cells which express 12-LOX mRNA and proteins. As shown in FIG. 8A, BHPP and compound 314 induced strong DNA fragmentation and apoptotic death of A431 cells. In contrast, BHPP and other compounds did not have any effect on the growth of normal human umbilical vein endothelial cells (FIGS. 8B–8F).

Compounds targeted to inhibiting the mammalian 12-LOX, selectively kill rodent and human tumor cells without affecting normal vascular endothelial cells. These compounds also appear to kill human solid tumor cells. The nature of cell death has been confirmed by multiple measurements to be apoptosis. Preliminary experiments demonstrate that the treatment of tumor cells with these compounds results in a decrease in the Bcl-2 (an anti-apoptotic molecule) protein prior to the initiation of cell death. It appears that apoptosis of tumor cells may also be selectively induced in vivo.

It is intended that the foregoing description be only illustrative of the present invention and that the present invention be limited only by the hereinafter appended claims.

We claim:

1. An in vitro method for determining effectiveness of a compound in producing apoptosis which comprises:
   (a) providing tumor cells which are known to produce 12-lipoxygenase, using normal cells as a control;
   (b) exposing the tumor cells and the normal cells to a compound which inhibits 12-lipoxygenase which is to be tested in vitro in a culture medium, wherein the compound is selected from the group consisting of:
      (1) a cyclic hydroxamic acid;
      (2) an aryl aliphatic acid;
      (3) nordihydro-guaiaretic acid, (NDGA);
      (4) N-benzyl-N-hydroxy-5-phenylpentanamide (BHPP);
      (5) baicalein; and
      (6) an antisense segment of DNA which selectively binds to DNA encoding 12-lipoxygenase; and
   (c) determining if the tumor cells have undergone apoptosis as a result of the exposure to the 12-lipoxygenase inhibiting compound, without producing apoptosis in the normal cells.

2. The method of claim 1 wherein the apoptosis is determined by measuring an extent of fragmentation of DNA in the cells.

3. The method of claim 1 wherein the apoptosis is determined visually by microscopy.

4. The method of claim 3 wherein the microscopy is by an electron microscope.

5. The method of claim 3 wherein the microscopy is by a light microscope.

6. The method of any one of claims 1, 2 or 3 wherein the apoptosis is determined by a flow cytometry separation of living and non-living cells.

7. The method of any one of claims 1, 2 or 3 wherein the tumor cells are rat mammary gland tumor cells.

8. The method of any one of claims 1, 2 or 3 wherein the tumor cells are rat mammary adenocarcinoma cells.

9. The method of any one of claims 1, 2 or 3 wherein the tumor cells are rat basophilic leukemia cells.

10. The method of any one of claims 1, 2 or 3 wherein the tumor cells are human erythroleukemia cells.

11. The method of any one of claims 1, 2 or 3 wherein the tumor cells are human epidermoid carcinoma cells.

12. The method of any one of claims 1, 2 or 3 wherein the compound is selected from the group consisting of nordihydro-guaiaretic acid, (NDGA) and N-benzyl-N-hydroxy-5-phenylpentanamide (BHPP).

13. The method of any one of claims 1, 2 or 3 wherein the compound is selected from the group consisting of a cyclic hydroxamic acid of the formula:

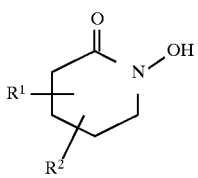

wherein $R^1$ is $C_1$ to $C_{24}$ alkyl and wherein $R^2$ is benzyl; and

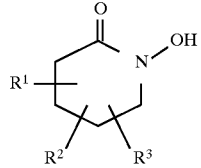

$R^1$, $R^2$ and $R^3$ each, independently, is hydrogen, C1–24 alkyl, C2–24 alkenyl or a group of the formula:

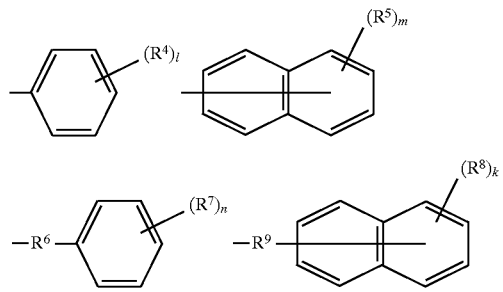

wherein
   $R^4$, $R^5$, $R^7$ and $R^8$ each, independently is hydrogen, C1–4 alkyl, C1–4 alkoxy, trifluoromethyl, halogen or nitro;
   1 is 1–3;
   m is 1–3;
   n is 1–3;
   k is 1–3;
   $R^6$ and $R^9$ each, independently is C1–24 alkylene or C2–24 alkenylene;
   with the proviso that, more than one of $R^1$, $R^2$ and $R^3$ are not hydrogen at the same time; and the pharmaceutically acceptable salts thereof;
   and an aryl aliphatic acid of the formula:

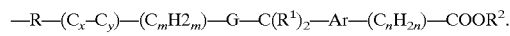

—R—($C_x$–$C_y$)—($C_mH2_m$)—G—C($R^1$)$_2$—Ar—($C_nH_{2n}$)—COOR$^2$.

wherein m and n are an integer between 1 and 6;
   wherein the pattern of substitution in the aryl ring (Ar) is selected from the group consisting of orth-, meta- and para-,
   wherein G is selected from the group consisting of O and S;
   wherein ($C_x$–$C_y$) is selected from the group consisting of ethynylene, cis-vinylene, trans-vinylene, propadienylene, and arylene;
   wherein R is selected from the group consisting of heptyl, octyl, nonyl, decyl, undecyl, dodecyl, tridecyl, tetradecyl, phenyl, benzyl, phenethyl, phenylpropyl, phenylbutyl, and phenylpentyl and isomers thereof;
   wherein each $R^1$ is independently H or lower alkyl or a combination thereof;
   wherein $R^2$ is H, a salt, lower alkyl or aralkyl.

14. A method for inducing selective apoptosis of tumor cells which comprises:

contacting the tumor cells and the normal cells used as a control with an amount of the compound which inhibits 12-lipoxygenase until apoptosis is induced in the tumor cells, wherein apoptosis is induced in the tumor cells without inducing apoptosis in the normal cells, wherein the compound is selected from the group consisting of:
(1) a cyclic hydroxamic acid;
(2) an aryl aliphatic acid;
(3) nordihydro-guaiaretic acid, (NDGA);
(4) N-benzyl-N-hydroxy-5-phenylpentanamide (BHPP);
(5) baicalein; and
(6) an antisense segment of DNA which selectively binds to DNA encoding 12-lipoxygenase.

15. The method of claim 14 which is in vitro.

16. The method of claim 14 wherein the apoptosis is determined by measuring an extent of fragmentation of DNA in the tumor cells.

17. The method of claim 14 wherein the apoptosis is determined visually by microscopy.

18. The method of claim 14 wherein the microscopy is by an electron microscope.

19. The method of claim 14 wherein the microscopy is by a light microscope.

20. The method of any one of claims 14 or 15 wherein the apoptosis is determined by a flow cytometry separation of living and non-living cells.

21. The method of any one of claims 14 or 15 wherein the tumor cells are rat mammary gland tumor cells.

22. The method of any one of claims 14 or 15 wherein the tumor cells are rat mammary adenocarcinoma cells.

23. The method of any one of claims 14 or 15 wherein the tumor cells are rat basophilic leukemia cells.

24. The method of any one of claims 14 or 15 wherein the tumor cells are human erythroleukemia cells.

25. The method of any one of claims 14 or 15 wherein the tumor cells are human epidermoid carcinoma cells.

26. The method of any one of claims 14 or 15 wherein the compound is selected from the group consisting of a cyclic hydroxamic acid of the formula:

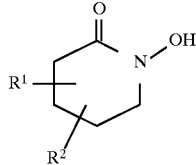

wherein $R^1$ is $C_1$ to $C_{24}$ alkyl and wherein $R^2$ is benzyl; and

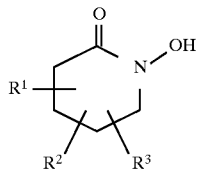

$R^1$, $R^2$ and $R^3$ each, independently, is hydrogen, C1–24 alkyl, C2–24 alkenyl or a group of the formula:

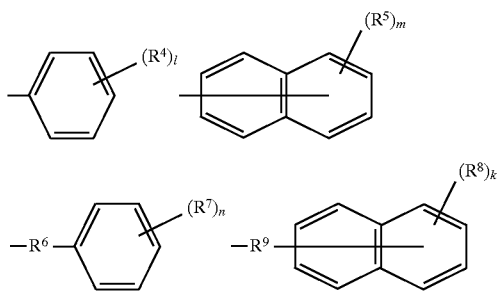

wherein
$R^4$, $R^5$, $R^7$ and $R^8$ each, independently is hydrogen, C1–4 alkyl, C1–4 alkoxy, trifluoromethyl, halogen or nitro;
1 is 1–3;
m is 1–3;
n is 1–3;
k is 1–3;
$R^6$ and $R^9$ each, independently is C1–24 alkylene or C2–24 alkenylene;
with the proviso that, more than one of $R^1$, $R^2$ and $R^3$ are not hydrogen at the same time; and the pharmaceutically acceptable salts thereof;
and an aryl aliphatic acid of the formula:

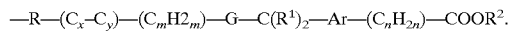

$$-R-(C_x-C_y)-(C_mH2_m)-G-C(R^1)_2-Ar-(C_nH_{2n})-COOR^2.$$

wherein m and n are an integer between 1 and 6;
wherein the pattern of substitution in the aryl ring (Ar) is selected from the group consisting of orth-, meta- and para-,
wherein G is selected from the group consisting of O and S;
wherein ($C_x$–$C_y$) is selected from the group consisting of ethynylene, cis-vinylene, trans-vinylene, propadienylene, and arylene;
wherein R is selected from the group consisting of heptyl, octyl, nonyl, decyl, undecyl, dodecyl, tridecyl, tetradecyl, phenyl, benzyl, phenethyl, phenylpropyl, phenylbutyl, and phenylpentyl and isomers thereof;
wherein each $R^1$ is independently H or lower alkyl or a combination thereof;
wherein $R^2$ is H, a salt, lower alkyl or aralkyl.

27. The method of claim 24 wherein the normal cells are present with the tumor cells.

28. A kit for detecting tumor cell apoptosis by a test compound which is to be tested using normal cells as a control and tumor cells which produce 12-lipoxygenase, which comprises:
(a) a known compound which induces apoptosis in the tumor cells without inducing apoptosis in the normal cells, wherein the compound is selected from the group consisting of:
(1) a cyclic hydroxamic acid;
(2) an aryl aliphatic acid;
(3) nordihydro-guaiaretic acid, (NDGA);
(4) N-benzyl-N-hydroxy-5-phenylpentanamide (BHPP);
(5) baicalein; and
(6) an antisense segment of DNA which selectively binds to DNA encoding 12-lipoxygenase; and (b) detection means for determining that apoptosis has been induced by the test compound as compared to the known compound in the tumor cells without producing apoptosis in the normal cells.

29. The kit of claim 28 wherein the detection means shows fragmentation of cell DNA in the tumor cells and the normal cells.

30. The kit of claim 28 wherein the detection means is microscopy.

31. The kit of claim 28 wherein the detection means can be used with flow cytometry.

32. The kit of claim 28 wherein the compound is selected from the group consisting of nordihydro guaiaretic acid (NDGA) and N-benzyl-N-hydroxy-5-phenylpentanamide (BHPP).

33. The kit of claim 28 wherein the compound is selected from the group consisting of a cyclic hydroxamic acid of the formula:

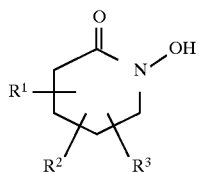

and an aryl aliphatic acid of the formula:

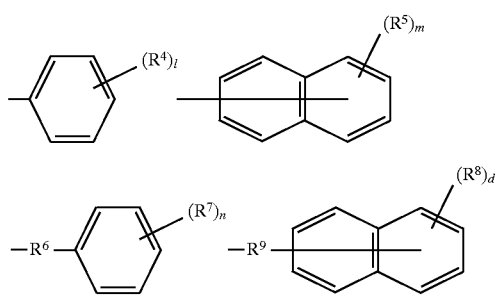

wherein $R^1$ is $C_1$ to $C_{24}$ alkyl and wherein $R^2$ is benzyl; and

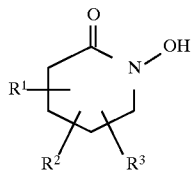

$R^1$, $R^2$ and $R^3$ each, independently, is hydrogen, C1–24 alkyl, C2–24 alkenyl or a group of the formula:

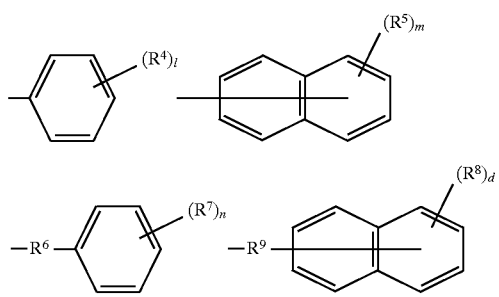

wherein $R^4$, $R^5$, $R^7$ and $R^8$ each, independently is hydrogen, C1–4 alkyl, C1–4 alkoxy, trifluoromethyl, halogen or nitro;

1 is 1–3;

m is 1–3;

n is 1–3;

k is 1–3;

$R^6$ and $R^9$ each, independently is C1–24 alkylene or C2–24 alkenylene;

with the proviso that, more than one of $R^1$, $R^2$ and $R^3$ are not hydrogen at the same time; and the pharmaceutically acceptable salts thereof;

and an aryl aliphatic acid of the formula:

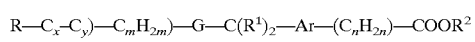

wherein m and n are an integer between 1 and 6;

wherein the pattern of substitution in the aryl ring (Ar) is selected from the group consisting of orth-, meta- and para-, wherein G is selected from the croup consisting of O and S;

wherein $(C_x–C_y)$ is selected from the group consisting of ethynylene, cis-vinylene, trans-vinylene, propadienylene, and arylene;

wherein R is selected from the group consisting of heptyl, octyl, nonyl, decyl, undecyl, dodecyl, tridecyl, tetradecyl, phenyl, benzyl, phenethyl, phenylpropyl, phenylbutyl, and phenylpentyl and isomers thereof;

wherein each $R^1$ is independently H or lower alkyl or a combination thereof;

wherein $R^2$ is H, a salt, lower alkyl or aralkyl.

34. A test system for inducing, detecting and comparing tumor cell apoptosis by a compound to be tested which comprises:

(a) normal cells which are used as a control;

(b) tumor cells to be tested which are known to express 12-lipoxygenase;

(c) a known compound which induces apoptosis in the tumor cells without inducing apoptosis in the normal cells, wherein the test compound is compared to the known compound in inducing apoptosis, wherein the compound is selected from the group consisting of:

(1) a cyclic hydroxamic acid;

(2) an aryl aliphatic acid;

(3) nordihydro-guaiaretic acid, (NDGA);

(4) N-benzyl-N-hydroxy-5-phenylpentanamide (BHPP);

(5) baicalein; and (6) an antisense segment of DNA which selectively binds to DNA encoding 12-lipoxygenase; and (d) means for determining the effectiveness in producing apoptosis of the compound to be tested compared to the known compound.

* * * * *